(12) United States Patent
Sachs

(10) Patent No.: US 12,364,542 B2
(45) Date of Patent: Jul. 22, 2025

(54) METHOD AND SYSTEM OF DORSAL ROOT GANGLION STIMULATION

(71) Applicant: Adam Sachs, Ottawa (CA)

(72) Inventor: Adam Sachs, Ottawa (CA)

(*) Notice: Subject to any disclaimer, the term of this patent is extended or adjusted under 35 U.S.C. 154(b) by 845 days.

(21) Appl. No.: 17/072,322

(22) Filed: Oct. 16, 2020

(65) Prior Publication Data

US 2021/0030488 A1    Feb. 4, 2021

Related U.S. Application Data

(63) Continuation-in-part of application No. PCT/CA2019/000051, filed on Apr. 17, 2019.

(60) Provisional application No. 62/658,718, filed on Apr. 17, 2018.

(51) Int. Cl.
| | | |
|---|---|---|
| *A61N 1/375* | (2006.01) | |
| *A61B 6/00* | (2006.01) | |
| *A61B 6/12* | (2006.01) | |
| *A61B 17/00* | (2006.01) | |
| *A61B 17/70* | (2006.01) | |
| *A61B 34/20* | (2016.01) | |
| *A61N 1/05* | (2006.01) | |
| *A61N 1/36* | (2006.01) | |

(52) U.S. Cl.
CPC ............. *A61B 34/20* (2016.02); *A61B 6/12* (2013.01); *A61B 6/487* (2013.01); *A61B 17/00234* (2013.01); *A61B 17/7001* (2013.01); *A61N 1/0558* (2013.01); *A61N 1/36062* (2017.08); *A61N 1/37518* (2017.08); *A61B 2017/00349* (2013.01); *A61B 2034/2046* (2016.02)

(58) Field of Classification Search
CPC .............. A61N 1/37518; A61N 1/3752; A61N 1/0558; A61N 1/375; A61N 1/36062
See application file for complete search history.

(56) References Cited

U.S. PATENT DOCUMENTS 7,736,191 B1 * 6/2010 Sochor .................. H01R 24/58
607/116

* cited by examiner

*Primary Examiner* — George R Evanisko
(74) *Attorney, Agent, or Firm* — Young Basile Hanlon & MacFarlane, P.C.

(57) ABSTRACT

A system and method of neurostimulation that is coupled with spinal fixation or the spine, implanted at the time of spine surgery, and allowing for a delayed minimally invasive connection to a stimulation source. The components of the system include the conduit anchor that secures to the instrumentation or spine; conduit housing through which leads enter and channels are isolated; the conduit cap to protect the implant; the lead adaptor entry port, wherein leads enter and channels are isolated; the lead adaptor pin housing, which contains contact pins; the keyed MIS tube, through which the lead adaptor is implanted in a second surgery; a grooved applicator to assist with lead placement; and an encircling clip to assist in securing a lead. The method of generating a signal in the frequency domain is described. The method of minimally invasive stimulation trial placement is described.

9 Claims, 23 Drawing Sheets

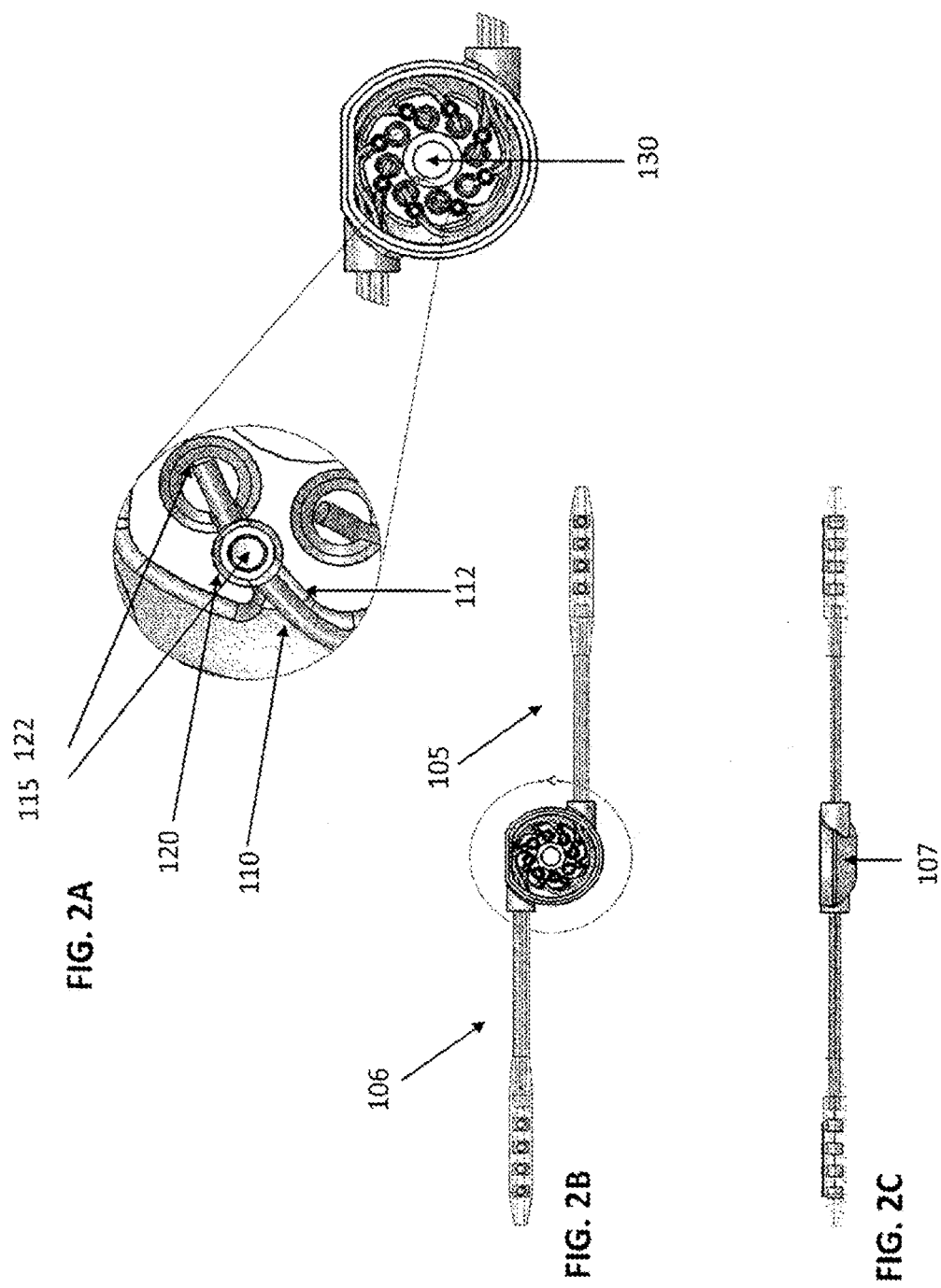

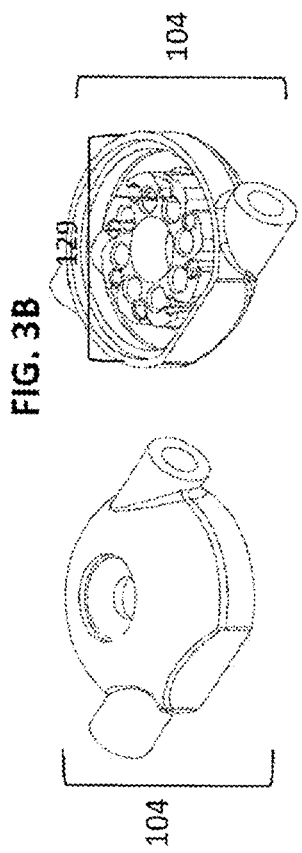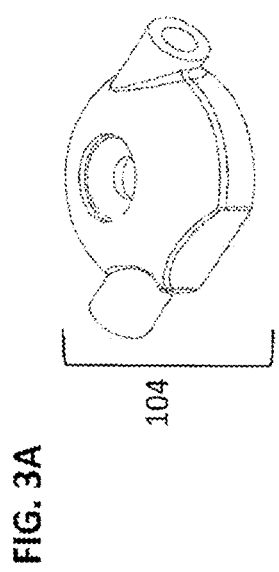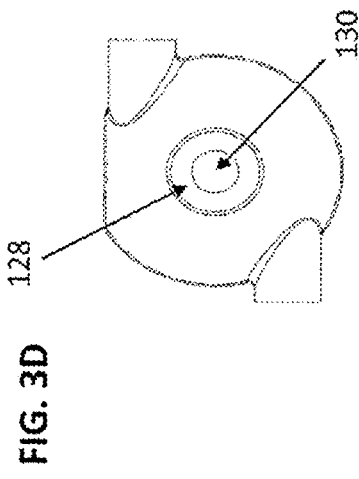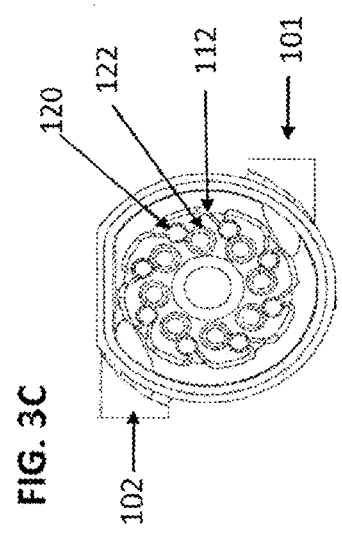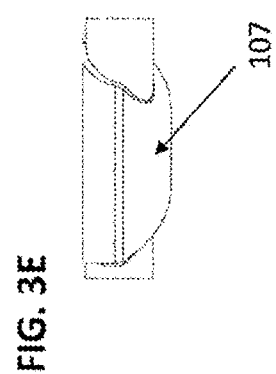

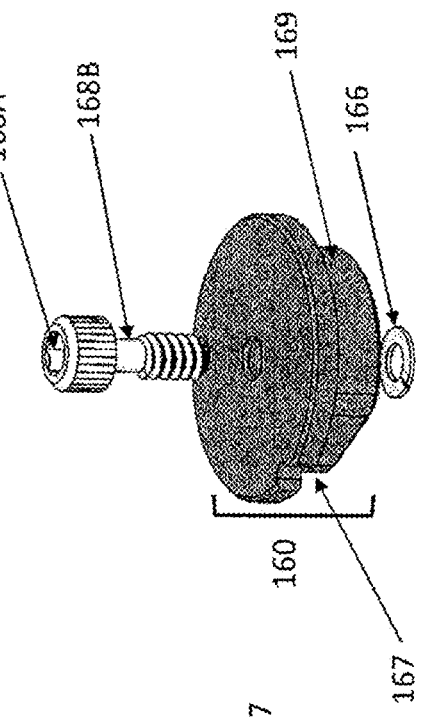
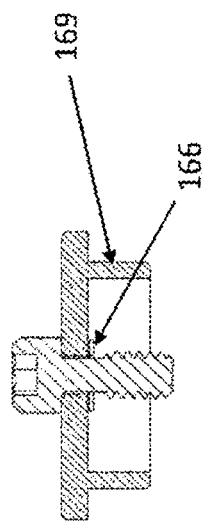
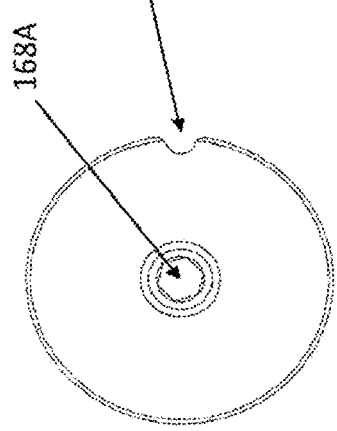
FIG. 5B
FIG. 5C
FIG. 5A

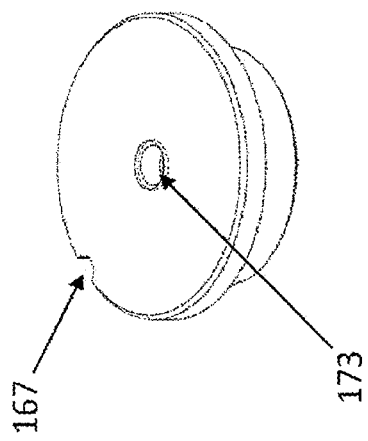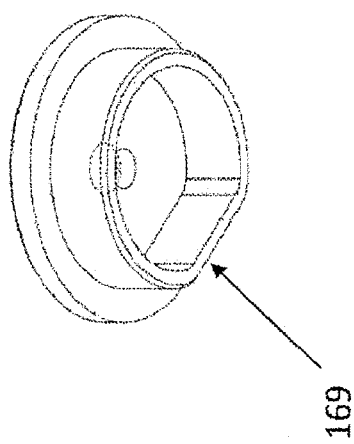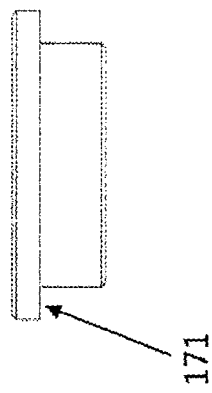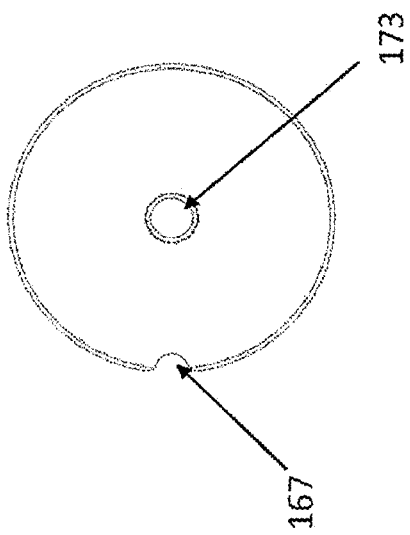

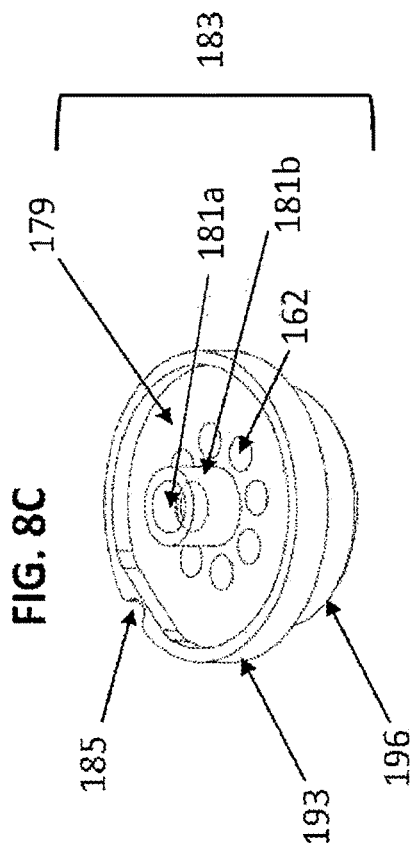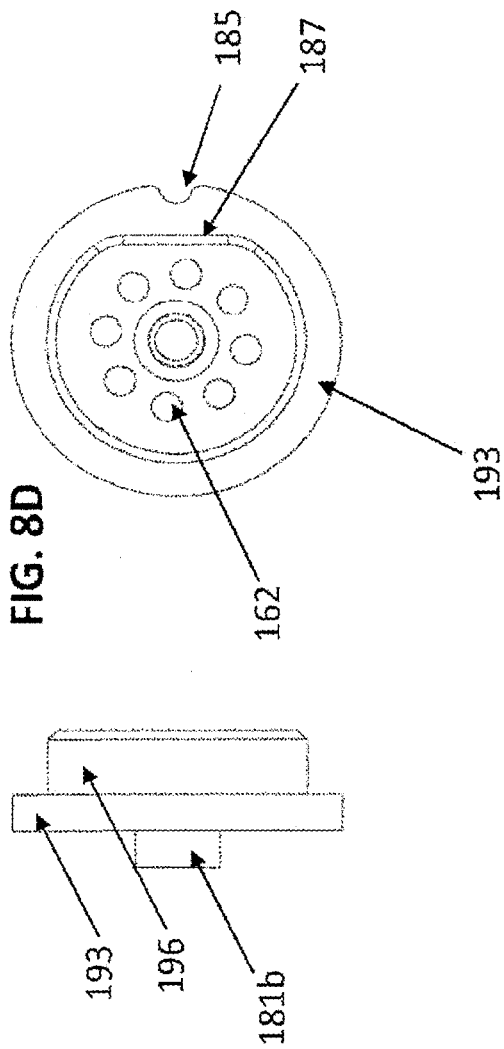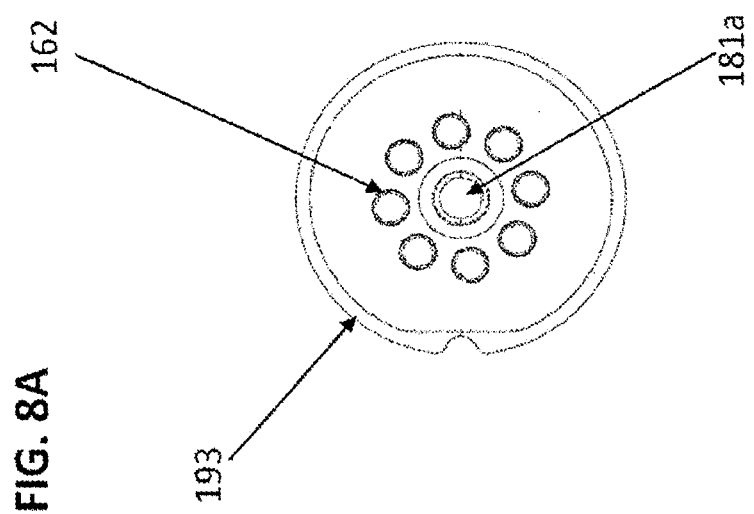

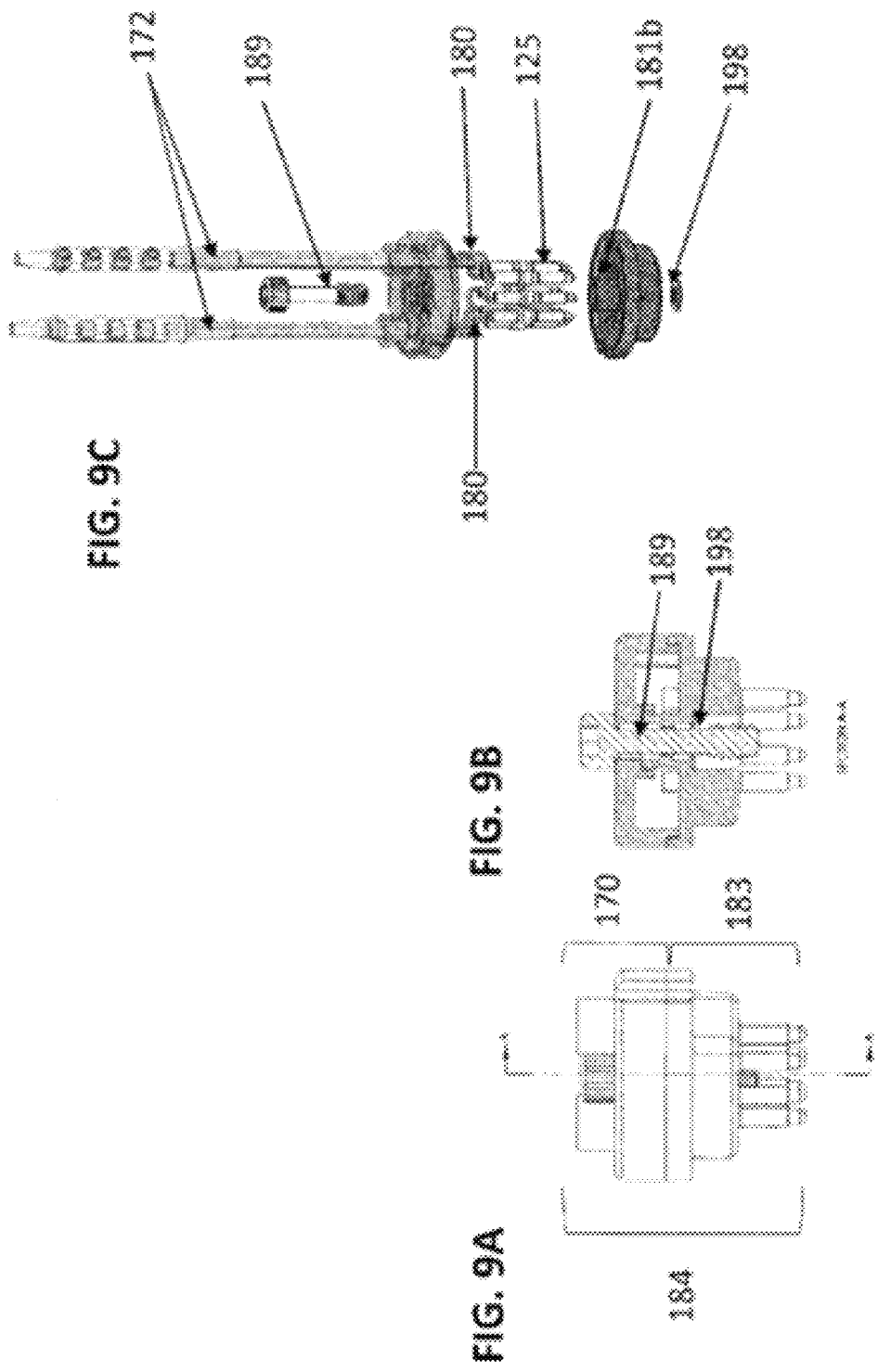

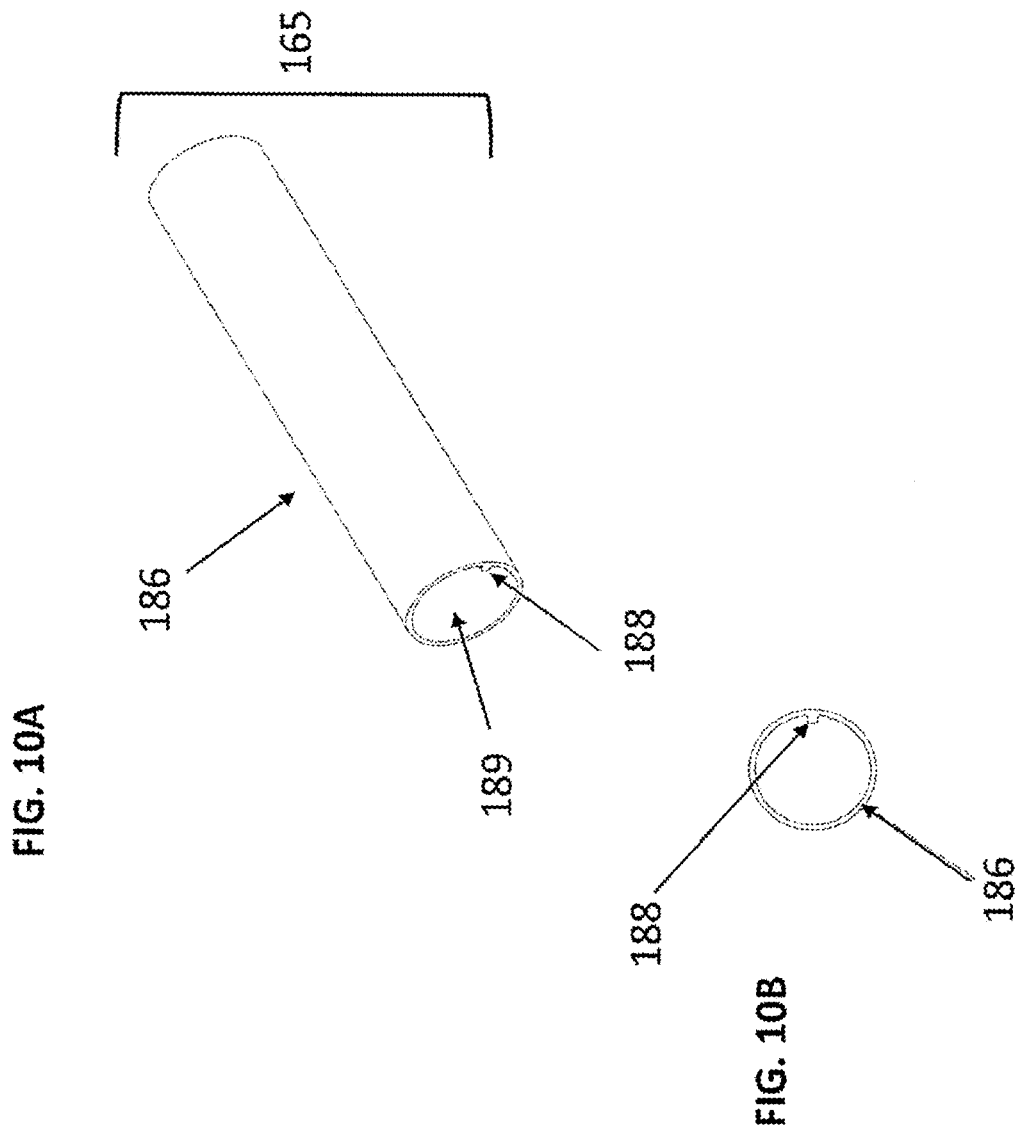

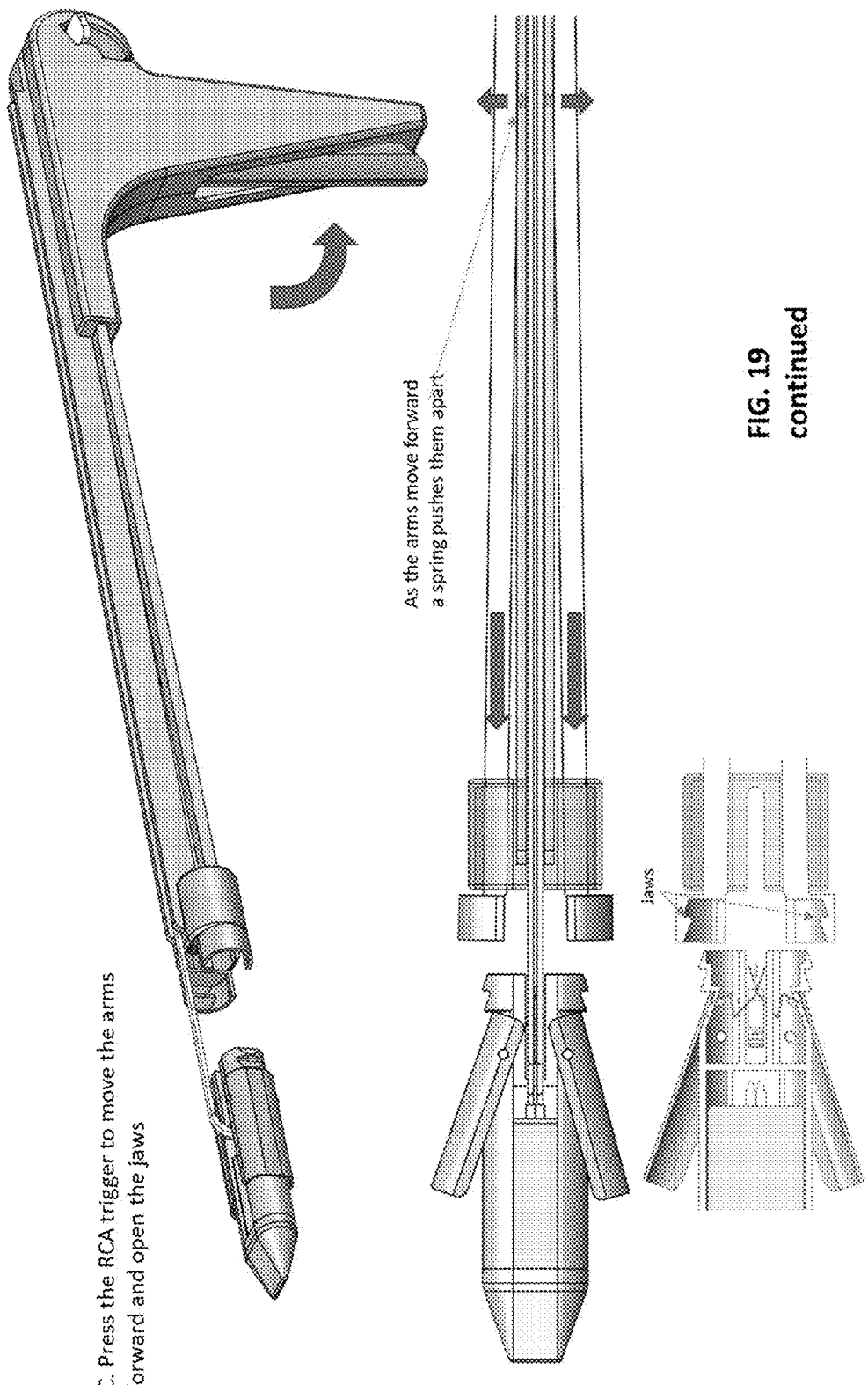

METHOD AND SYSTEM OF DORSAL ROOT GANGLION STIMULATION

CROSS-REFERENCE TO RELATED APPLICATION(S)

This application is a continuation-in-part of PCT/CA2019/000051 filed Apr. 17, 2019, which claims priority to and the benefit of U.S. Provisional Application Patent Ser. No. 62/658,718, filed Apr. 17, 2018, the entire disclosure of which is hereby incorporated by reference.

FIELD OF THE INVENTION

The present invention relates to spinal treatment, in particular coupling a clinical neurostimulator to a spinal fixation system.

BACKGROUND OF THE INVENTION

Typical neurosurgical methods for treating radicular pain include decompression, decompression and fusion (to maintain the decompression for a longer duration), and neuromodulation techniques such as spinal cord stimulation and dorsal root ganglion stimulation. The two strategies (decompression with or without fusion and neuromodulation) have largely remained separate and mutually exclusive for any given surgical intervention. Typically, a decompressive surgery is used when there is lumbar nerve root compression and no previous spine surgeries. Spinal cord or dorsal root ganglion (DRG) stimulation is used to treat neuropathic pain such as that seen in Chronic Regional Pain Syndrome, in which there is an absence of a significant component of spinal nerve root compression. When neuropathic pain arises from spinal nerve root compression in a person who has had previous spinal surgery at that level, there is controversy as to the best neurosurgical approach—some neurosurgeons will perform a redo spinal decompression and supplement it with fusion, others use a neuromodulation approach with spinal cord stimulation. DRG stimulation is not typically used because in the current state of the art it is deployed by a percutaneous system done without an open exposure, and scar tissue from the previous surgery makes it difficult and dangerous to provide this therapy without an open surgical exposure. However, a number of redo decompression and fusion surgeries fail and require spinal cord stimulation (a form of neuromodulation), and a number of spinal cord stimulators fail because of inadequate spinal fixation or decompression. Furthermore combining the two approaches is difficult because a) spinal cord stimulation is usually done at a different level (lower thoracic) than the corresponding nerve roots that are involved (lumbar) for a decompression, b) there no good way in the current state of the art of anchoring DRG stimulation in an open spine surgery, c) overlapping two distinct systems (one electrical, one mechanical) would complicate the surgery and any potential surgical revisions thereafter, d) there is an historical, training-based, and cultural separation between spine surgeons who perform fusions and functional neurosurgeons who perform neuromodulation and e) neuromodulation typically requires a percutaneous trial, which cannot be achieved in a delayed fashion following recovery from spinal fusion using the current state of the art. The trial stimulation would need to be delayed during surgical recovery—because patients with pain often fluctuate in the level of pain and are unreliable to report response to a neuromodulation trial in the months following an open decompression and fusion.

Therefore there is a need in die art for a surgically simple system that integrates neuromodulation for neuropathic pain with the hardware used in spinal fusion or the spine itself, allowing simple adoption by spine-trained surgeons, neurostimulation at the level of surgery, and the ability' to integrate a minimally invasive surgical (MIS) trial which can be delayed after recovery (or even indefinitely).

SUMMARY OF THE INVENTION

The present invention provides a system for integrating neuromodulation in the form of dorsal root ganglion (DRG), nerve root or spinal cord stimulation with a spinal screw fixation system in which the neuromodulation system is coupled with the spinal fixation by connecting to either die rod, the screw head, screw cap (blocker) or the spine itself, and allowing for a delayed trial via an MIS system for attaching the internal pulse generator extension lead cable (hereafter referred to as "lead"). The main components of the system are:

Conduit housing, in which stimulator leads enter via the entry ports and individual channels are isolated, locked in place and distributed in the same plane.

A conduit anchor that is bonded or screwed to the conduit housing and forms the roof of the conduit. It contains a keyed seal ring to connect to the internal pulse generator extension adaptor in a unique configuration via a specialized percutaneous MIS system. The anchor connects to the rod, screw, screw cap or spine. The conduit housing and conduit anchor when bonded, are collectively referred to as the conduit.

An implanted conduit cap with a central perforation, which is threaded into the screw head and mounts on top of the conduit anchor in order to protect the circuitry and the screw head from scar tissue, and allow the MIS connection of the lead adaptor to the conduit. It is also keyed such that it secures into the conduit anchor in a single orientation, and can be removed through the keyed MIS tube.

The lead adaptor entry port in which the leads that connect to an internal pulse generator enter and multiple channels are distributed to surface contacts on the face, which connect directly to the contacts on the opposing face of the conduit anchor. There is a central hole allowing a partially threaded screw to connect it to the conduit. It is keyed to allow the channels to match in a unique configuration.

The lead adaptor pin housing which is bonded to the lead adaptor entry—port and forms the floor of the lead adaptor. It is keyed to allow a unique fit. Each channel from the leads connects to a pin which passes through holes in the pin housing. The lead adaptor entry port and the lead adaptor pin housing, when bonded are collectively referred to as the lead adaptor. A keyed MIS tube which passes over a keyed dilator and mounts onto the ring on tire conduit anchor. An embodiment has a grooved applicator which assists in placing leads, and may also have an encircling clip which clips onto a rod and helps secure a lead.

A system and method of neurostimulation that is coupled with spinal fixation or the spine, implanted at the time of spine surgery, and allowing for a delayed minimally invasive connection to a stimulation source. The components of the system include the conduit anchor that secures to the instrumentation or spine; conduit housing through which leads enter and channels are isolated; the conduit cap to protect the implant; the lead adaptor entry' port, wherein leads enter and channels are isolated; the lead adaptor pin housing, which contains contact pins; the keyed MIS tube, through which the lead adaptor is implanted in a second surgery; a grooved applicator to assist with lead placement; and an encircling clip to assist in securing a lead. The method of generating a signal in the frequency domain is described. The method of minimally invasive stimulation trial placement is described.

A system for the purpose of placing stimulator leads on neural elements during a spine surgery is described, allowing anchoring the system to a rigid stable construct, and using a minimally invasive surgery at a later date to access and stimulate the system comprising: a conduit housing; a conduit anchor; a keyed MIS tube; a lead adaptor entry port; and a lead adaptor pin housing. A further embodiment comprises a keyed MIS tube concept. A further embodiment comprises a grooved applicator for placing leads and/or an encircling clip to secure a lead.

Accordingly, in certain embodiments, there is provided a system for placement of stimulator leads on neural elements during a spine surgery, anchoring the system to a rigid stable construct, and using a minimally invasive surgery at a later date to access and stimulate the system comprising: a. a conduit housing comprising ports for stimulator leads; b. a conduit anchor for connection to the spine or spine instrumentation, wherein said conduit housing and said conduit anchor, when connected, form a conduit; c. a keyed minimally-invasive surgery (MIS) tube, wherein said MIS tube is for mounting on said conduit anchor and through which a lead adaptor is implanted in said minimally invasive surgery; and d. said lead adaptor, wherein said lead adaptor comprises a lead adaptor entry port for entry of said stimulator leads and a lead adaptor pin housing comprising contact pins. In specific embodiments, the system further comprising a conduit cap. In specific embodiments, the system further comprising a grooved applicator for placing leads. In specific embodiments, the system further comprising an encircling clip to secure a lead.

In certain embodiments, there is provided a method comprising the steps of decompressing neural elements, securing the conduit to the instrumentation or spine, placing a stimulator lead, mating the lead to the conduit, and securing the conduit cap. An embodiment has the further step of implanting fixation screws to the spine. An embodiment has the further step of securing a rod. An embodiment has the further step of repeating steps e) and f). An additional embodiment has the additional steps of making an incision into the skin, surgical navigation or fluoroscopy, docking a needle in a conduit cap screw head, removing central stylet of needle, placing a guide wire, sequentially dilating using surgical dilators, placing a keyed MTS tube, passing a tool through the keyed MIS tube to loosen a screw, removing the conduit cap, passing the lead adaptor through the keyed MIS tube, locking the lead adaptor to the conduit, and removing the keyed MIS tube.

In certain embodiments, there is provided a system for inserting an internal puke generator (IPG) battery in a patient, said system comprising a cap/dissector for attachment to a IPG housing, said cap/dissector for dissecting through tissue to a fascia layer; a IPG housing, said IPG housing sized to accommodate a IPG for insertion and further comprising a means to secure said IPG housing to a fascia layer; said IPG housing for releasable connection to an insertion tool comprising a main housing and a trigger assembly connected to said main housing, wherein activation of said trigger assembly causes said IPG housing to release from said main housing.

In certain embodiment, there is provided a method of inserting an IPG in a patient, said method comprising: connecting an IPG is connected to leads; sliding said IPG into an IPG housing; securing a cap/dissector to said IPG housing to produce a IPG housing assembly; inserting the IPG housing assembly into the insertion tool; dissecting through tissue with front of the cap to the fascia layer; securing the IPG housing assembly to the fascia layer; releasing the IPG housing assembly from said insertion tool, and optionally suturing the IPG housing assembly in place.

In certain embodiments, there is provided an IPG housing assembly comprising an IPG housing comprising an IPG and a cap. In specific embodiments, the IPG housing assembly is a unitary structure.

In certain embodiment, there is provided a system for inserting an internal pulse generator (IPG) battery in a patient, said system comprising a tool, said tool comprising a main housing for releasable connection to an IPG housing assembly and a trigger assembly connected to said main housing, wherein activation of said trigger assembly causes said IPG housing to release from said main housing. In specific embodiments, the system further comprises: a cap/dissector for attachment to an IPG housing, said cap/dissector for dissecting through tissue to a fascia layer; a IPG housing, said IPG housing sized to accommodate a IPG for insertion and further comprising a means to secure said IPG housing to a fascia layer, wherein said IPG housing comprising an IPG and having said cap/dissector attached forms said IPG housing assembly. In certain embodiments, the system further comprises an IPG housing assembly comprising an IPG housing comprising an IPG and a cap.

In certain embodiments, there is also provided a method of signal generation for stimulating neural elements using frequency domain stimulation is disclosed comprising the steps of: creating an amplitude signal; defining the phase; generating the frequency function; and computing the inverse Fourier transform to obtain the desired stimulation signal.

BRIEF DESCRIPTION OF THE FIGURES

FIG. 2A shows a detail view of the conduit housing with the leads and channels in place, according to an embodiment of the invention;

FIG. 2B shows a plan view of the conduit housing with the leads and channels in place, according to an embodiment of the invention;

FIG. 2C shows an elevation view of the conduit housing with the leads and channels in place, according to an embodiment of the invention;

FIG. 3A shows a perspective view of the bottom of the conduit housing without the lead, according to an embodiment of the invention;

FIG. 3B shows a perspective view of the top of the conduit housing without the lead, according to an embodiment of the invention:

FIG. 3C shows a plan view of the conduit housing without the lead, according to an embodiment of the invention;

FIG. 3D shows a plan view of the bottom of the conduit housing without the lead, according to an embodiment of the invention;

FIG. 3E shows an elevation view of the conduit housing without the lead, according to an embodiment of the invention;

FIG. 5A shows a plan view of the conduit cap, in an embodiment of the present invention;

FIG. 5B shows an exploded view of the conduit cap, in an embodiment of the present invention;

FIG. 5C shows a cross-sectional view of the conduit cap, in an embodiment of the present invention;

FIG. 6A shows a plan view of the conduit cap without the screw, in an embodiment of the invention.

FIG. 6B shows an elevation view of the conduit cap without the screw, in an embodiment of the invention.

FIG. 6C shows a perspective view of the top of the conduit cap without the screw, in an embodiment of the invention.

FIG. 6D show's a perspective view of the bottom of the conduit cap without the screw, in an embodiment of the invention.

FIG. 8A shows a plan view of the bottom of the lead adaptor pin housing, according to an embodiment of the present invention, FIG. 8B show an elevation view of the lead adaptor pin housing, according to an embodiment of the present invention;

FIG. 8C shows a perspective view of the top of the lead adaptor pin housing, according to an embodiment of the present invention;

FIG. 8D shows a plan view of the top of the lead adaptor pin housing, according to an embodiment of the present invention;

FIG. 9A shows an elevation view showing the lead adaptor, according to an embodiment of the present invention;

FIG. 9B shows a cross-sectional view showing the lead adaptor according to an embodiment of the present invention;

FIG. 9C shows an exploded view showing the lead adaptor, according to an embodiment of the present invention;

FIG. 10A shows a plan view of the keyed MIS tube, according to an embodiment of tire present invention, FIG. 10B shows a perspective view of the keyed MTS tube, according to an embodiment of the present invention;

DETAILED DESCRIPTION

A method and system of stimulating the spinal cord, dorsal root ganglion (DRG), or nerve roots, at multiple levels is disclosed. The system is connected to the spinal instrumentation or spine and allows for a minimally-invasive surgery (MIS) trial and connection to an internal pulse generator is described. This system may be used by spine surgeons at the time of spine surgery in cases in which the surgeon considers a high probability of ongoing neuropathic pain following spinal decompression and fusion such as in patients who have had previous spinal surgery at that level.

Method Of DRG Stimulation

Figure 15:
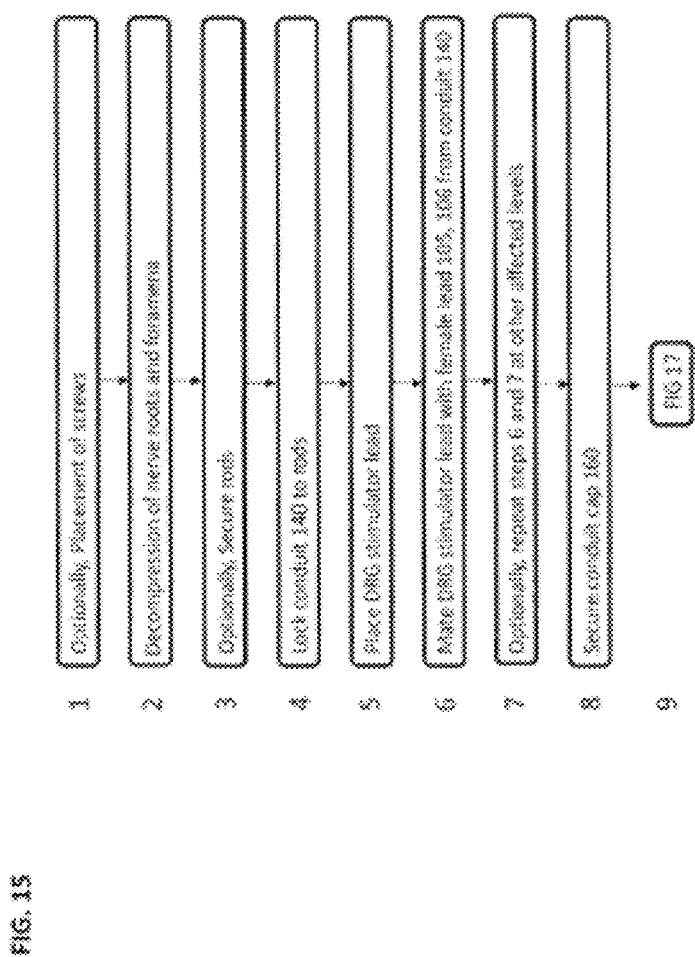
FIG. 15 shows the steps of the initial surgical implant of the conduit and conduit cap with a dorsal root ganglion stimulator; according to an embodiment of the present invention.

Initial surgical implantation—dorsal root ganglion (DRG) stimulation (with reference to FIG. 15): Optionally, fixation screws such as pedicle screws are used to fix spinal segments into a certain position (step 1). Following placement of screws, the nerve roots and neural foramens are decompressed (step 2). Optionally, the surgeon would secure the rods in place with screw caps (step 3). Tn step 4, the surgeon then locks the conduit (via the conduit anchor) to the spinal instrumentation (eg. rod or screw head) or spine (eg. a spinous process) in step 5, the surgeon then places the DRG stimulator lead with the lead end over die DRG, and the male connector end mates into the female connector of the extension lead that runs into the conduit (step 6). Steps 5 and 6 are repeated at each level in which stimulation may be desirable (step 7). A boot may be necessary' for sealing. In step 8, the surgeon secures the conduit cap over the conduit. Wound closure proceeds in the usual.

Figure 16:
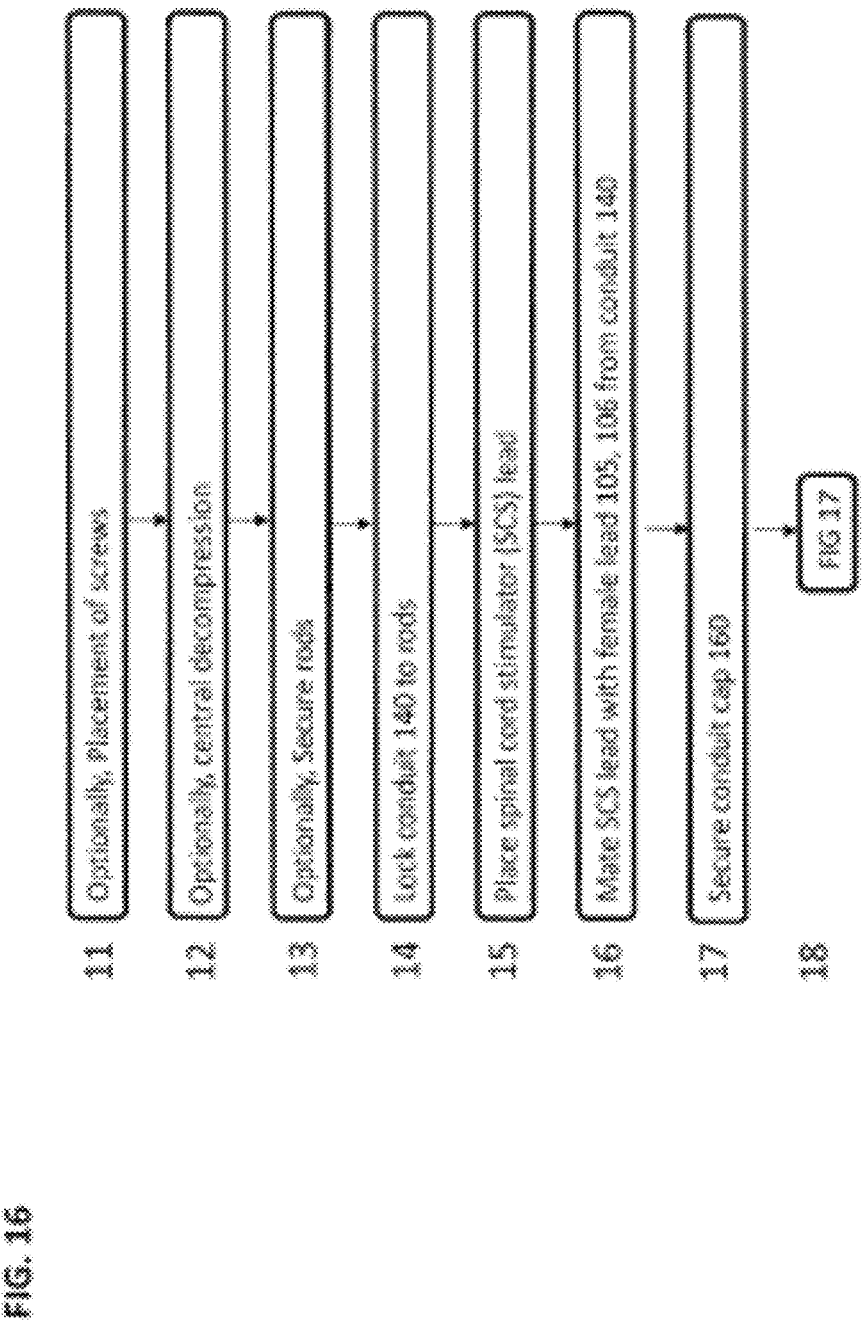
FIG. 16 shows the steps of the initial surgical implant of the conduit and conduit cap with a spinal cord stimulator; according to an embodiment of the present invention.

Initial Surgical Implantation—Spinal Cord Stimulator (SCS): With reference to FIG. 16, in the case of thoracolumbar or cervical decompression and fusion, the surgeon has access to the lower spinal cord. In this case the surgeon may elect to use SCS. Optionally, fixation screws are placed in step 11, and central decompression is done in step 12. Optionally, the surgeon secures the rods in place with screw caps in step 13. In step 14, the surgeon then locks the conduit (via the conduit anchor) to the spinal instrumentation (e.g. rod or screw head) or spine (e.g. a spinous process). In step 15 the spinal cord stimulator lead is placed in step 16, the male connector end of the SCS lead(s) mates into the female connector of the lead(s) (that runs into the conduit. A boot may be necessary' for sealing. Finally, in step 17 the surgeon secures a conduit cap over the conduit. Wound closure proceeds in the usual.

Figure 17:
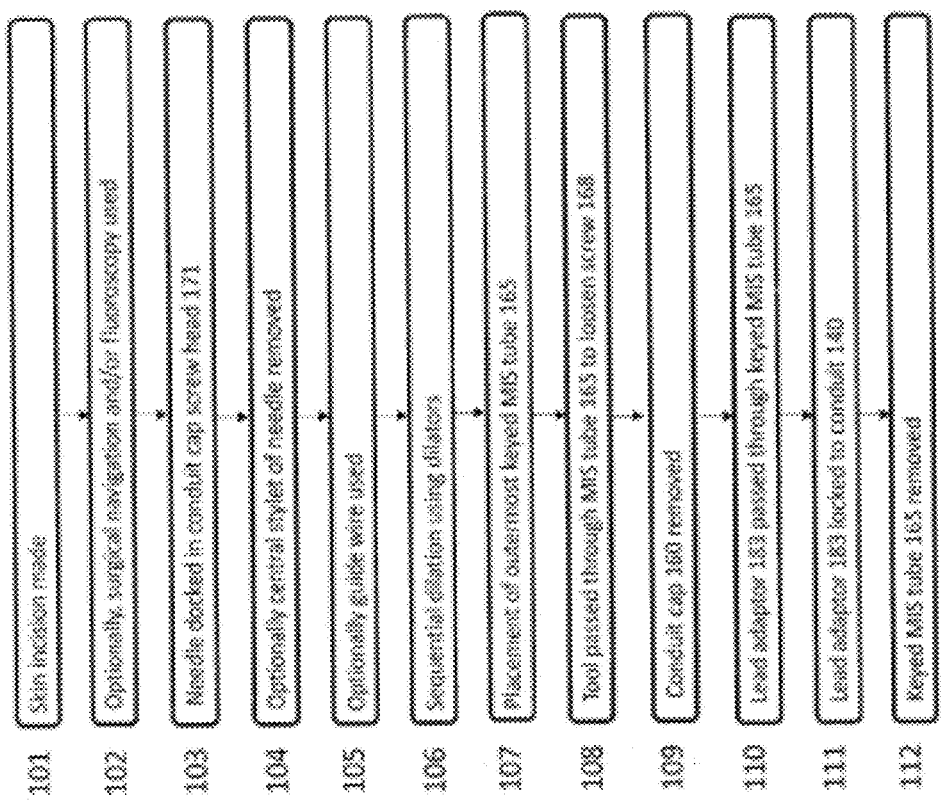
FIG. 17 shows the steps of the second MIS surgical implant of the lead adaptor; according to an embodiment of the present invention.

Second Surgery at a Subsequent Date—MIS placement of lead adaptor: With reference to FIG. 17, following recovery from spine surgery (described above) if the patient has ongoing neuropathic pain, the surgeon may perform a trial of stimulation or may proceed with a permanent stimulation implant using a minimally invasive surgical (MIS) technique specifically designed for use with this system. In step 101: L small (approx. 1-2 cm) skin incision is made. Optionally, surgical navigation or fluoroscopy is used (step 2). A needle such as a Jamshidi needle is inserted to dock in the screw head of the conduit cap (step 103). Optionally, the central stylet is removed (step 104). Optionally a guide wire is inserted (step 105). In step 106, sequential dilation with surgical dilators is done. In step 107 the inner dilators are removed, and the outermost keyed MIS tube remains, leaving a surgical corridor around the conduit. In step 108, a tool such as a screwdriver or Allen key is passed through the MIS keyed tube and loosens the screw of the conduit cap. It may be necessary to use forceps or a pituitary' to remove the conduit cap (step 109). In step 110, the lead adaptor is passed through the keyed MIS tube in a order to align the contacts with the conduit. The partially threaded screw is then tightened to lock the lead adaptor to the conduit (step 11). The keyed MIS tube is then removed (step 12). The surgeon may then externalize or tunnel the distal end of the lead from the lead adaptor.

SYSTEM OF DRG STIMULATION—Description of System Components COMPONENT 1—the conduit housing 104 (with reference to FIGS. 1, 2A-C, 3A-E) contains entry ports 101, 102 (e.g., at least two ports) through which tine proximal end of a divided lead 105,106 passes. The individual channels 110 within the divided leads 105, 106 are isolated within the conduit housing 104. The conduit housing 104 comprises a dish 107 with one or more entry ports 101, 102 along its side adapted to receive a lead 105, 106. Within the dish 107, protruding upwardly from the base of the dish 107, is a plurality of radially arranged isolators 112. The isolators 112 are adapted to receive a single channel 110 each, and the channel I 10 may be attached to the isolators 112 by a connector 115, which may be a stud, laser welding, soldering, or any number of means known in the art. One skilled in the art would appreciate that the dish 107 may be round, rectangular or square in its opening 129, or any combination thereof.

With reference to FIGS. 1, 2A-C, 3A-E, in use, the leads 105, 106 are passed into the dish 107 through tire ports 102, 103, and the individual channels 110 are distributed, one to each isolator 112, and are retained there using the connector 115.

With reference to FIGS. 1, 2A-C, 3A-E, 12, The individual channels 110 are isolated and in an embodiment may be arranged radially and fixed with connectors 115 like fixations studs in an embodiment in a plane. In an embodiment, each isolated channel 110 passes through a channel lock 120 and terminates in a conductive chamber 122 in which the channel 110 is not insulated and may conduct with the pins 125 (shown in FIG. 2A) which functions as an intermediary conductive material. In an embodiment there is a central hole 130 to allow a screw 131 (with reference to FIG. 12) to fix the conduit housing 104 to the conduit anchor 132, together forming the conduit 140 (shown in FIG. 12). In an embodiment, on die undersurface of the conduit housing 104 there is an annular depression 128 surrounding the central hole 130 for the head of the screw 131 to fit in.

COMPONENT 2—with reference to FIGS. 4A-C, 12, the conduit anchor 132 allows the conduit 140 to connect to the spinal instrumentation or spine. The conduit anchor 132 generally comprises a disc portion 135 with a clamp 137 protruding from one edge of the disc portion 135. The disc portion 135 has a raised edge 142 and an annular seal of a flexible material (not shown) on the top of the raised edge 142, with a sunken floor 144 containing a central opening 145, preferably threaded. The floor 144 is perforated with a plurality of perforations 147. From one outer edge 148 of the disc portion 135 is a C-shaped clamp 137, comprising a lower hook 151 and an upper threaded aperture 152. The axis A of the threaded aperture 152 may be parallel to the axis B of the central opening 145 or, preferably, angles in towards the tip 154 of the lower hook 151. Preferably the clamp 137 is directed to retaining a rod (not shown). However, it is not limited to this use and may retain elements of the instrumentation or the spine itself. In an embodiment this may be through a clamp 137 that hooks under the instrumentation and a fastener 153 such as a nut or screw that passes through a threaded aperture 152 to apply pressure and fixate the conduit 140 to the instrumentation or spine. The conduit anchor 132 fits into the conduit housing 104 and has perforations 147 that align with the conductive chamber 122 of the conduit housing 104. It also contains a threaded hole 130 that will allow a screw 171, to connect the conduit cap 160 (shown in FIG. 5B) or the lead adaptor 184. In an embodiment in contains a keyed seal ring 163 comprising the raised edge 142 and key divot 164, that may form a seal with the keyed MIS tube 165 (shown in FIGS. 10A, B). This contains a key divot 164 that allows the MIS tube 165 to fit in a unique orientation. In an embodiment there may be a central opening 161 (preferably threaded) in the bottom surface of the disc 144 lo allow the conduit anchor 132 to be attached to die conduit housing 104. In an embodiment, the conduit may be manufactured using PEEK or a biologically inert metal such as titanium.

COMPONENT 3: With reference to FIGS. 5A, B, 6A-D, 9C, 10 12, tire conduit cap is shown 160. This is secured on top of the conduit 140 following the initial spinal surgery. The conduit cap 160 generally comprises a disc shape and has with a key notch 167 on the side and an inner annular protrusion 169 that projects below it that is adapted to form a seal with the conduit 140. The disc has an outer extent 171 beyond die annular protrusion 169 to help create a seal with the annular seal ring 163 of the conduit 140. It has a central shaft 173, and a partially threaded screw 168B to allow it to be secured to the central hole 145 of the conduit anchor 132. In an embodiment, a washer 166 is used to keep the screw 168B within tire conduit cap 160. There is an outer key notch 167 to allow alignment with the keyed MIS tube 165 (shown in FIG. 10) and an inner tubular structure with one or more flat edges acting as an inner key 169 that fits inside or outside the keyed seal ring 163 of the conduit 140. The conduit cap 160 sets up the alignment with the keyed MIS 165 tube that ultimately results in a unique configuration and alignment of the channels 180 (via the pins 125) of the lead adaptor 184 with the channels 110 of the conduit 140, shown in FIG. 12. The screw head 168A al lows a needle to be docked within it in step 103 of the MIS surgery' (with reference to FIG. 37)

COMPONENT 4—the Lead Adapter Entry Port 170. With reference to FIGS. 7A-D, 9A-C, 10A, B the lead adaptor entry port 170 is described. The lead adaptor entry port comprises a short cylindrical tube 174 opening into two or more smaller cylindrical entry ports 177 for the male half 172 of internal pulse generator leads on the side, a central hole 176 for the partially threaded screw 189 and a keyed notch 178 to fit into the key 180 of the keyed MIS tube 165. The proximal portion of the internal pulse generator leads 172 pass through the entry ports 177 after which each channel 180 is bonded to a conductive connector pin 125. This forms the roof of and will be bonded to (or screwed to), the lead adaptor pin housing 183. Collectively they form the lead adaptor 184.

COMPONENT 5: With reference to FIGS. 8A-D, 9A-C.7D, 12, the lead adaptor pin housing 183 generally comprises a dish 179 that fits with the bottom surface 182 of the lead adapter entry port 170. There is a short cylinder protruding below 196 with a plurality of apertures 162 through which conductive connector pins 125 pass. The cylinder contains one or more flat edges 187 to assist in the unique fitting into the conduit 140. Tn an embodiment the connector pins are spring loaded. There is a central column 181b that extends upward with a central hole 181a through which a screw 189 may pass. In an embodiment, a washer 198 is used to keep the screw 189 captive within the lead adaptor 184. This will allow the lead adaptor 184 to be connected during the second surgery to the conduit 140. There is an outer edge 193 that aligns with the lead adaptor entry port 170 and allows a seal to be made with die conduit 140. This also contains a keyed hole 185 to allow alignment within the outer edge 193

COMPONENT 6: With reference to FIGS. 10A, B, 11A, B, a keyed MIS tube 165 is cylindrical on the outside 186, but contains a protrusion 188 on the inside 189 such that it mounts on the conduit 140 in a unique configuration. In an embodiment it contains an O-ring (not shown) on the bottom to create a fluid seal. This will be used as an MTS surgical channel through which the main parts of the second stage of the surgery—(described in FIG. 17) is performed. It is also the final tube in a progressive dilator system (not shown in the figures). Therefore the second last tube will require an inner non-keyed cylinder (not shown) and an outer key hole (groove) through which the protrusion 188 will pass.

This keying is useful for any number of MIS surgeries in which mechanical or electrical components are required to align. The keying may either comprise a groove along the length of the inner wall 189 of the tube, with a corresponding protrusion on the outer wall of the component to be inserted into the tube 165, or it may comprise an inward protrusion (not shown) from the inner wall, which is engaged by a corresponding longitudinal groove (not shown) along the outer wall of the inner tube (or component to be inserted), or any plurality thereof.

Figure 1:
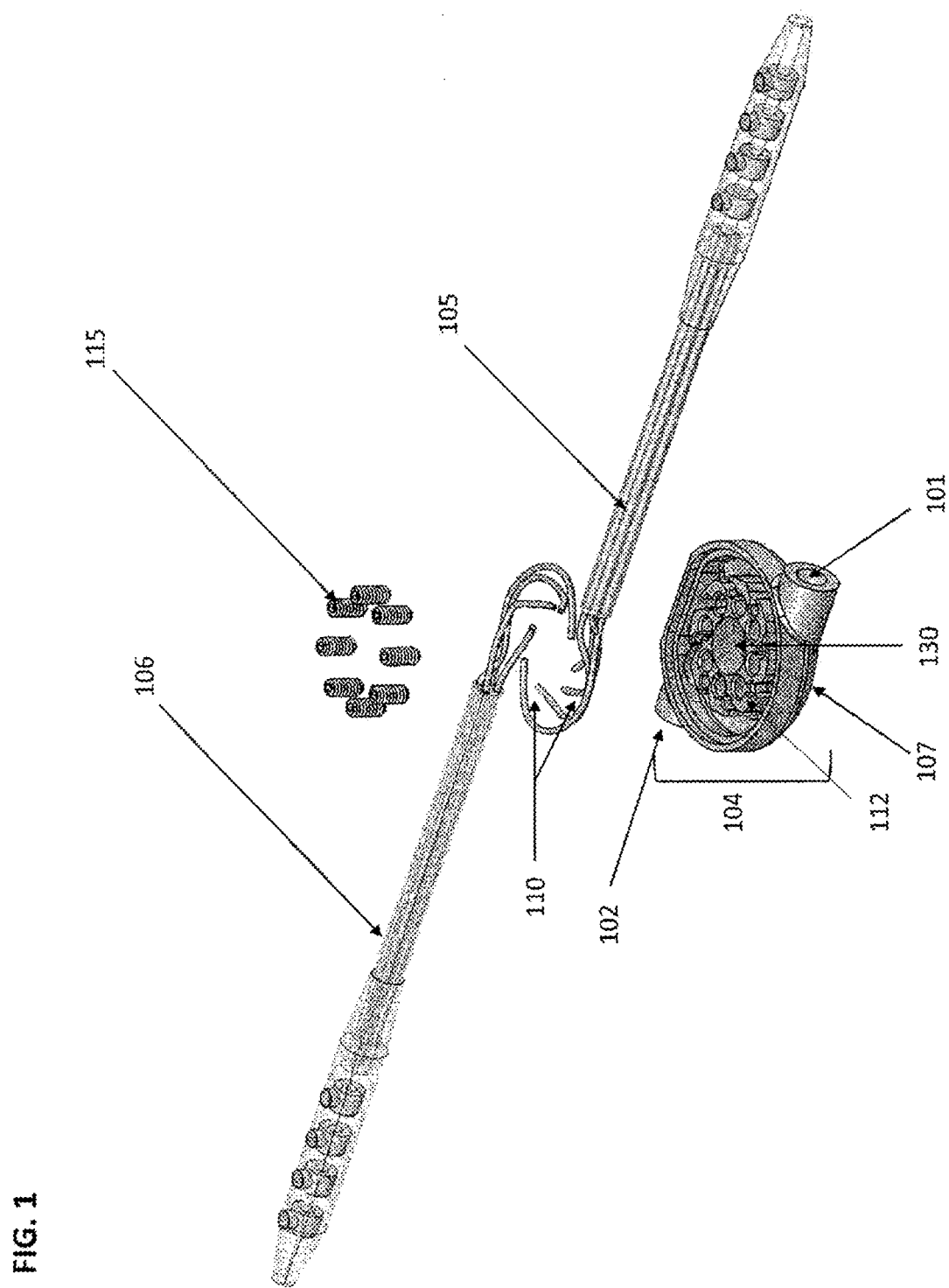
FIG. 1 shows an exploded view of the conduit housing, according to an embodiment of the invention.
Figure 4A:
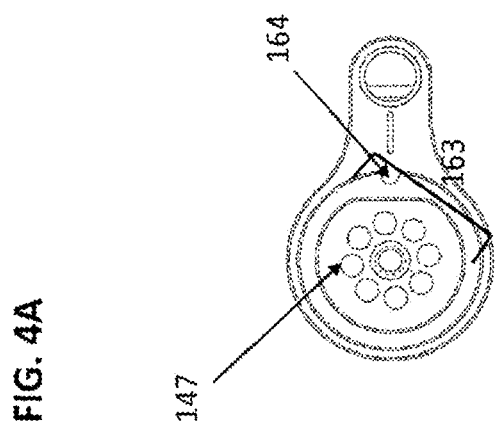
FIG. 4A shows a plan view of the conduit anchor, according to an embodiment of the invention.
Figure 4B:
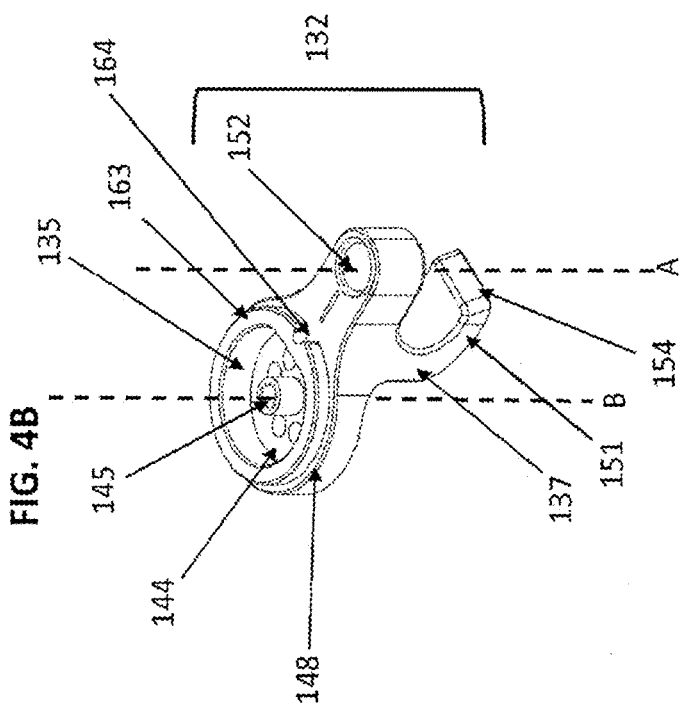
FIG. 4B shows a perspective view of the conduit anchor, according to an embodiment of the invention.
Figure 4C:
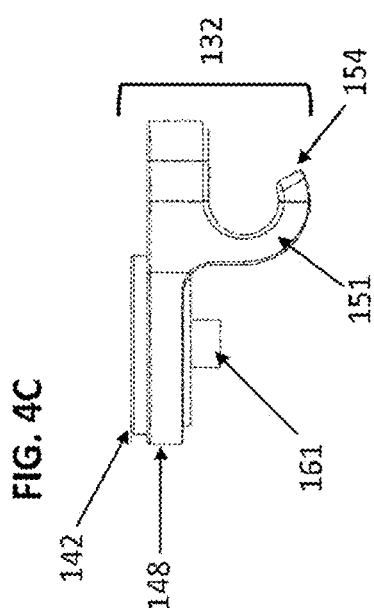
FIG. 4C shows an elevation view of the conduit anchor, according to an embodiment of the invention.
Figure 7C:
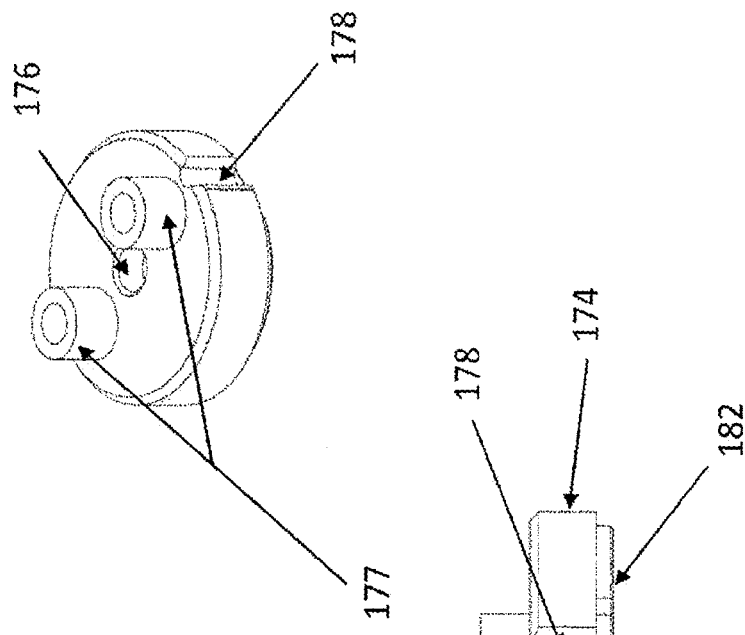
FIG. 7C shows a perspective view of the top of the lead adaptor entry' port, according to an embodiment of die present invention.
Figure 7D:
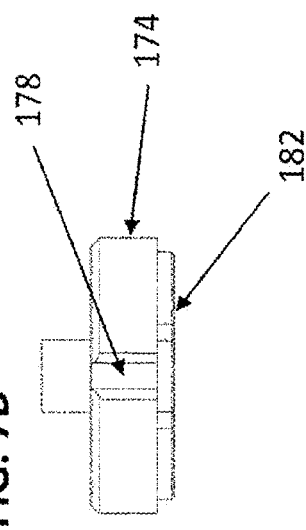
FIG. 7D shows an elevation view of the keyed notch of the lead adaptor entry port, according to an embodiment of the present invention.
Figure 7A:
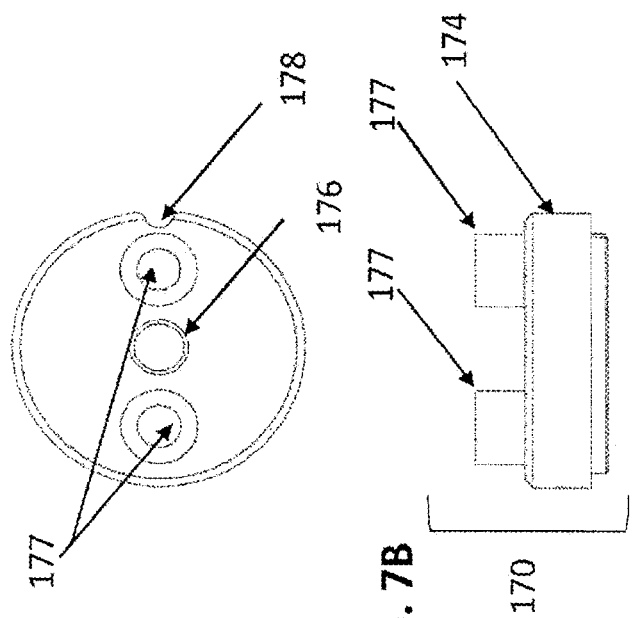
FIG. 7A shows a plan view of the lead adaptor entry port, according to an embodiment of the present invention.
Figure 7B:
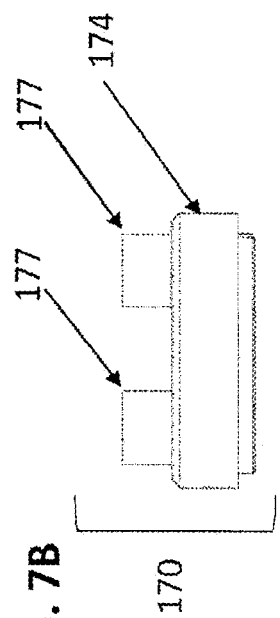
FIG. 7B shows an elevation view of the lead adaptor entry port, according to an embodiment of the present invention.
Figure 11B:
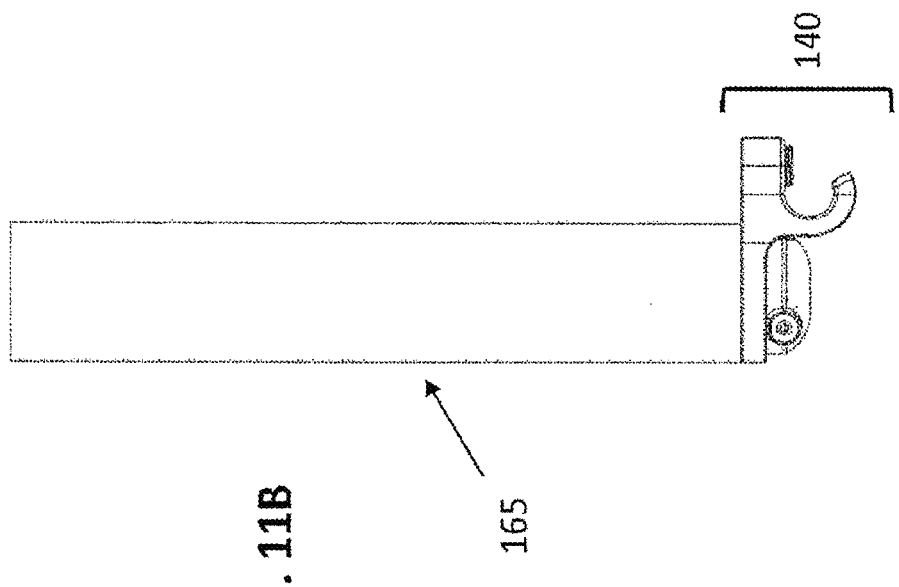
FIG. 11B shows an elevation view of the keyed MIS tube fit on top of the conduit anchor, with the anchor at the side; according to an embodiment of the procedure.
Figure 11A:
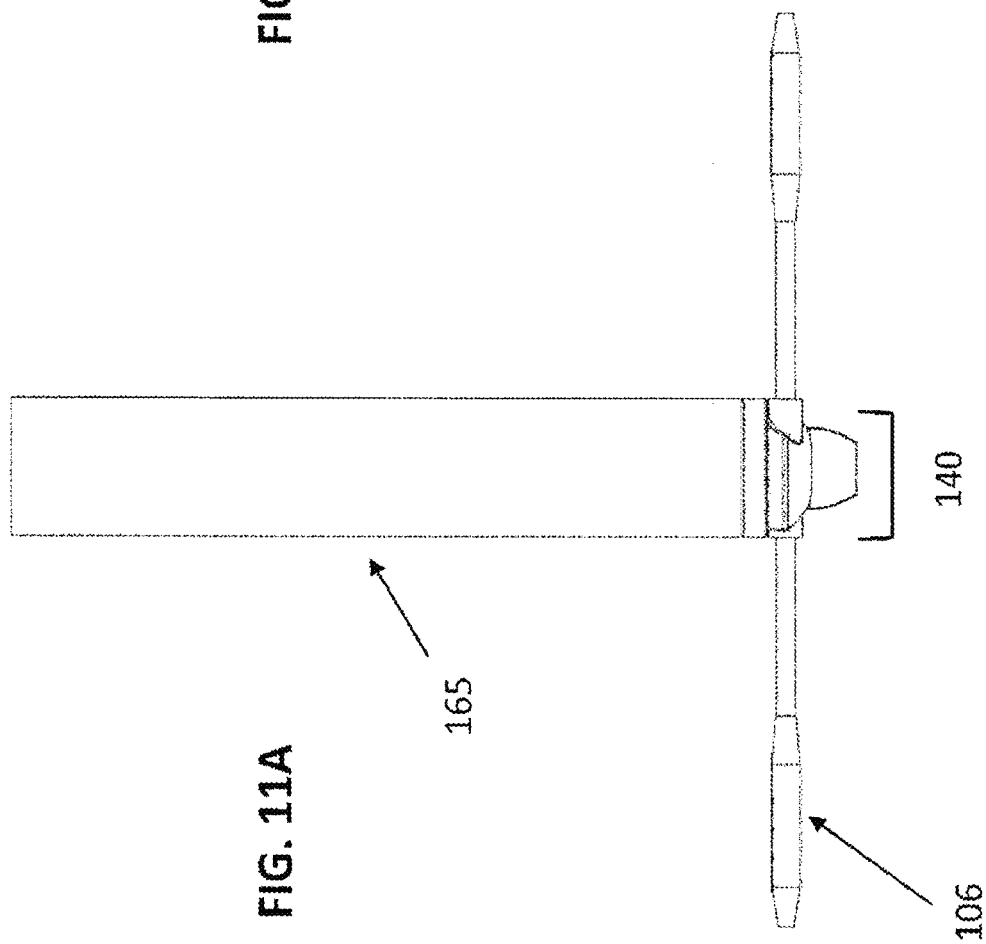
FIG. 11A shows an elevation view of the keyed MIS tube fit on top of the conduit anchor, with the anchor facing opposite; according to an embodiment of the procedure.
Figure 12:
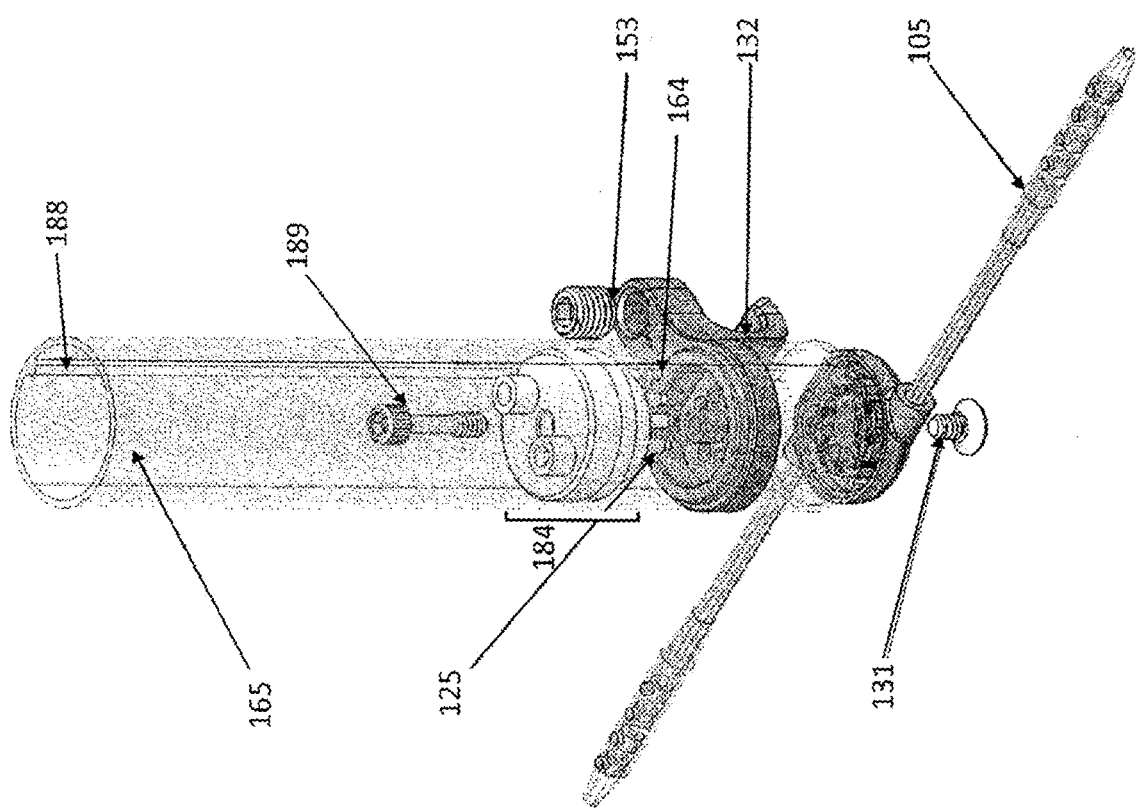
FIG. 12 shows an exploded view demonstrating the fit of tire conduit, lead adaptor and keyed MIS tube; according to an embodiment of the present invention.
Figure 13:
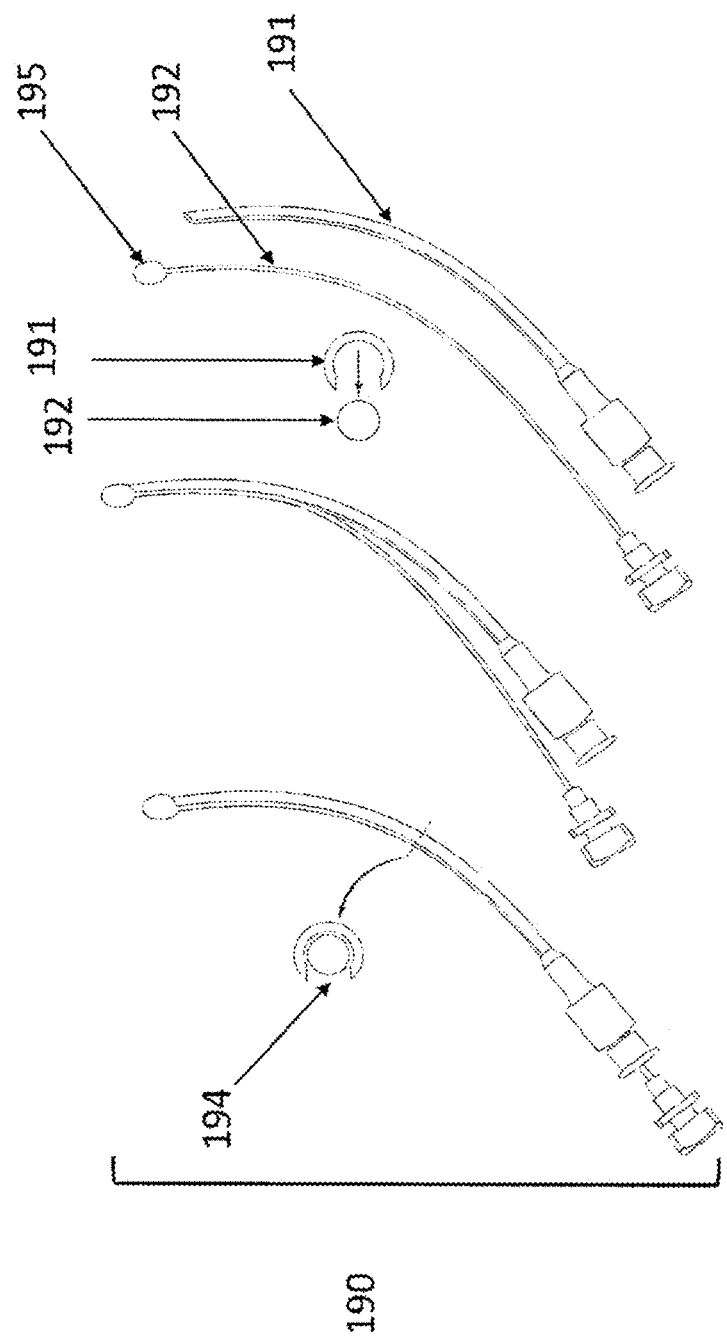
FIG. 13A shows the blunt ended curved placement needle with its two detachable components together; according to an embodiment of the present invention.
FIG. 13B shows the blunt ended curved placement needle with Us inner stylet being removed; according to an embodiment of the present invention.
FIG. 13C shows the blunt ended curved placement needle with its inner stylet removed; according to an embodiment of the present invention.
Figure 14:
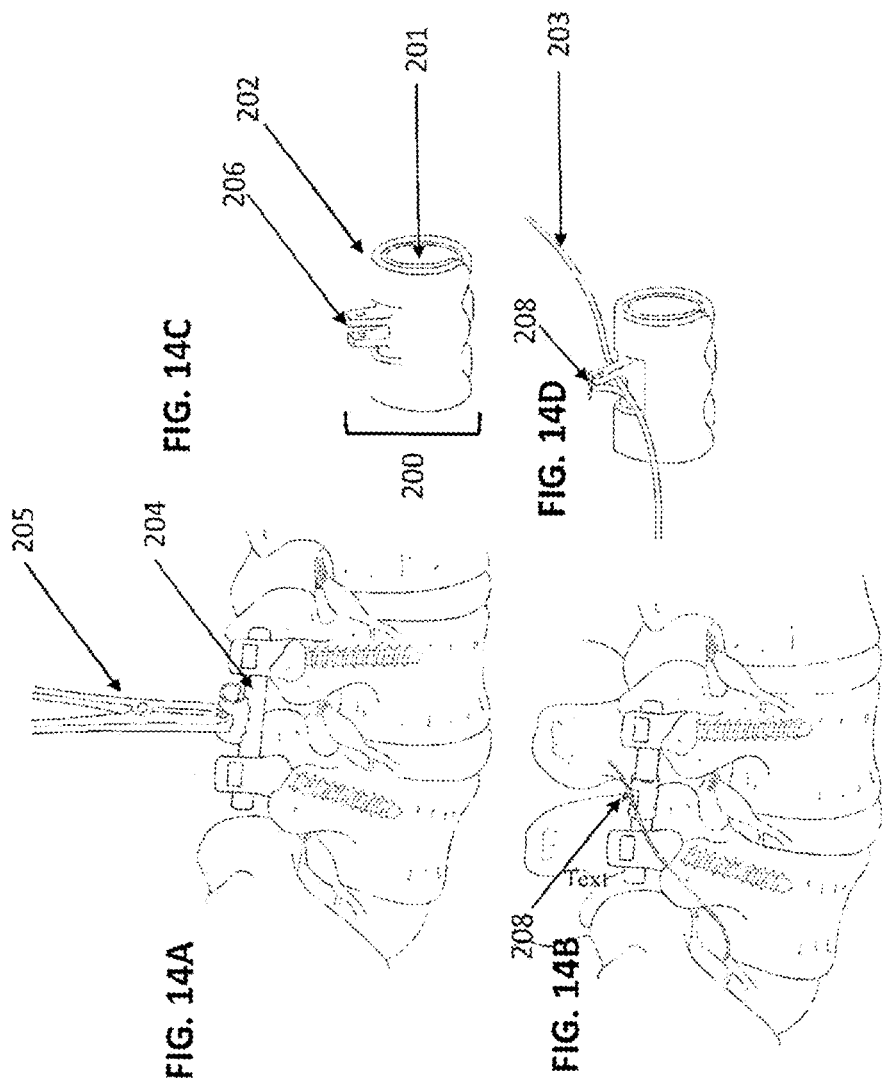
FIG. 14A shows a lead securing clip being applied to a rod allowing a lead to be secured to the instrumentation; according to an embodiment of the present invention.
FIG. 14B shows a lead securing clip secured to a rod with a lead to be secured by a suture; according to an embodiment of the present invention.
FIG. 14C shows a lead securing clip with its leaves unopposed; according to an embodiment of the present invention.
FIG. 14D shows a lead securing clip with its leaves being sutured together to secure a lead; according to an embodiment of the present invention.

COMPONENT 7: With reference to FIGS. 13A-C, to assist with placement of the stimulator in the neural foramen, a grooved applicator 190 comprising an external shaft 191 and internal stylet 192. and is described. The external shaft 191 will resemble a hollow-bore needle with an inner stylet 192, except the shaft 191 has a slit 194 along its length to allow removal of tire stylet 192 and placement of the stimulator lead (not shown). The slit may be on the concave side, the convex side, or anywhere in between. In an embodiment, the applicator 190 would be available with varying degrees of curvature (to accommodate variations in foramenal anatomy), would be semiflexible (likely plastic or rubber) and may have a blunt end 195 of the stylet 192 or external shaft 191 so as not to damage the neural elements.

COMPONENT 8: With reference to FIGS. 14A-D, ail encircling clip 200 is described with silicone or rubber on concave side 201 to increase friction that allows a lead 203 to be secured to tire rod 204 via an applicator 205. On the convex side 202, silicone leaflets 206 allow the lead 203 to be secured with a suture 208.

With reference to FIGS. 12, 9C, 4B, 4C, 2A, 1 the assembly of the components 1,2,4,5. and 6 is shown in an exploded view. The keyed tube 165 is arranged over the conduit anchor 132 by fitting around the raised edge 142 and sitting on the outer edge 148. The conduit housing 104 has one or more leads 105, 106 entering the ports 101, 102. The keyed MIS tube 165 is uniquely secured to the conduit anchor 132 by passing the protrusion 188 through the key divot 164 of the conduit anchor 132. The conduit anchor 132 fits over the conduit housing 104, such that the underside of the disc portion 162 engages with the opening of the dish 129 of the conduit housing 104. The C-shaped clamp 137 extends downwardly, alongside the edge of the dish. Above the conduit anchor is a lead adapter 184. The lead adaptor 184 engages the annular seal 163 of the raised edge 142 of the conduit anchor 132, and permits the pins 125 to electrically engage with the conductive chambers 122, providing electrical connections between the male side of the divided lead 172 and the female side of the divided lead 105, 106. These electrical connections are uniquely matched due to the necessary alignment of the keyed notch 178 and keyed hole 185 with the key divot 164 of the conduit anchor 132. This alignment is made necessary' by the protrusion 188 of the keyed MIS tube 165. The lead entry port 170 and lead adaptor 162 (which is bonded to the lead entry port T70) are secured to the conduit anchor 132 via a screw 189. Preferably, the extension leads are divided such that the female half is utilized in conjunction with the conduit, and the male half is used with the extension adaptor.

Optionally, the system further comprises an internal pulse generator (IPG)(i.e. computer components and battery) for the stimulation which is for implantation into the patient. In certain embodiments where an IPG is implanted, there is optionally provided an insertion tool and a method of inserting the IPG using the tool. In certain embodiments, the insertion tool allows for the IPG to be inserted using a single incision.

Insertion System and Method

The present invention further provides an IPG insertion system comprising an IPG insertion tool and a method of inserting an IPG using the tool. The insertion tool and method may be used in combination with the method of neurostimulation detailed above or other methods, including other methods of neurostimulation, requiring insertion of a battery or IPG.

Figure 18:
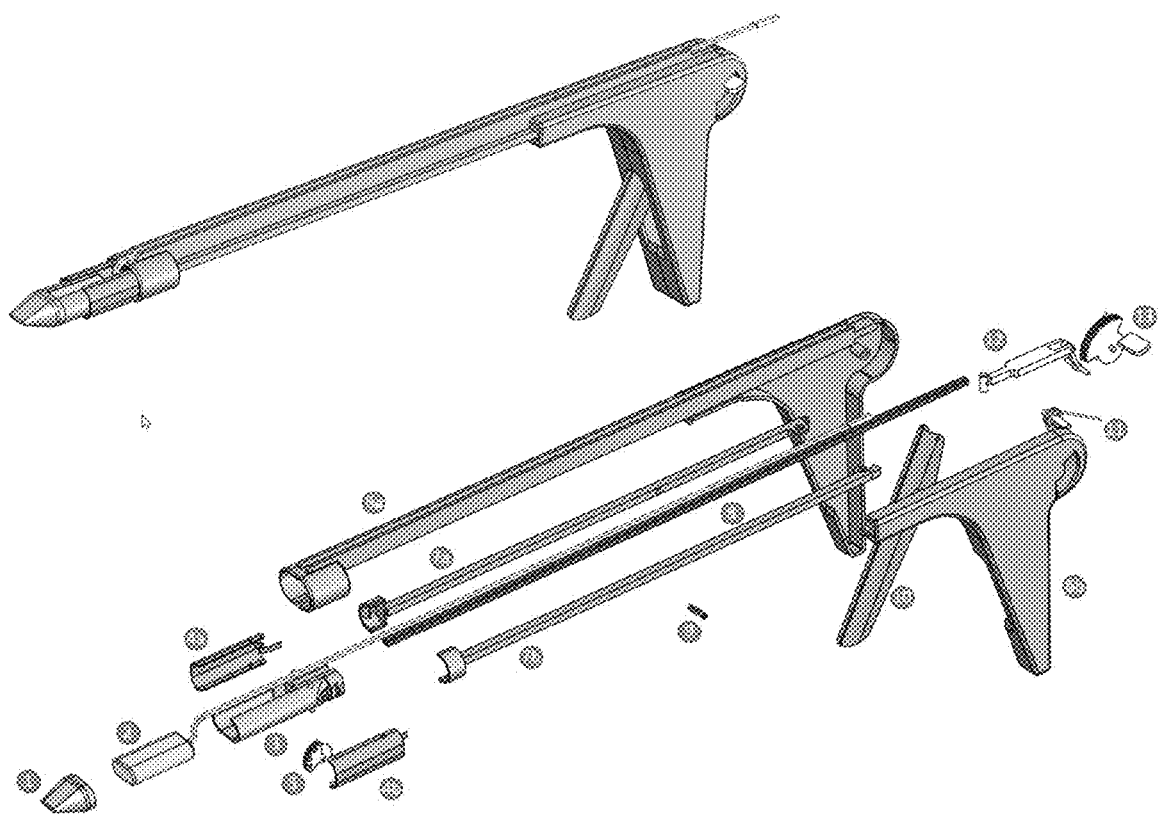
FIG. 18 shows an insertion system according to an embodiment of the invention.

With reference to FIG. 18, the insertion system comprises an IPG insertion tool and IPG housing assembly, the system comprises the following components (1) Cap/Dissector; (2) IPG with Leads; (3) IPG Housing; (4) Stabilizing Wings; (5) Locking Needle Assembly (LNA); (6) Main Housing; (7) Release/Capture Arms (RCA); (8) LNA Engagement Arm; (9) RCA Spring; (10) RCA Trigger; (11) RCA Trigger Spring; (12) RCA Trigger Mechanism; and (13) LNA Engagement Trigger. In certain embodiments, the system is a single use tool. In alternative embodiments, the system is re-usable.

Figure 19:
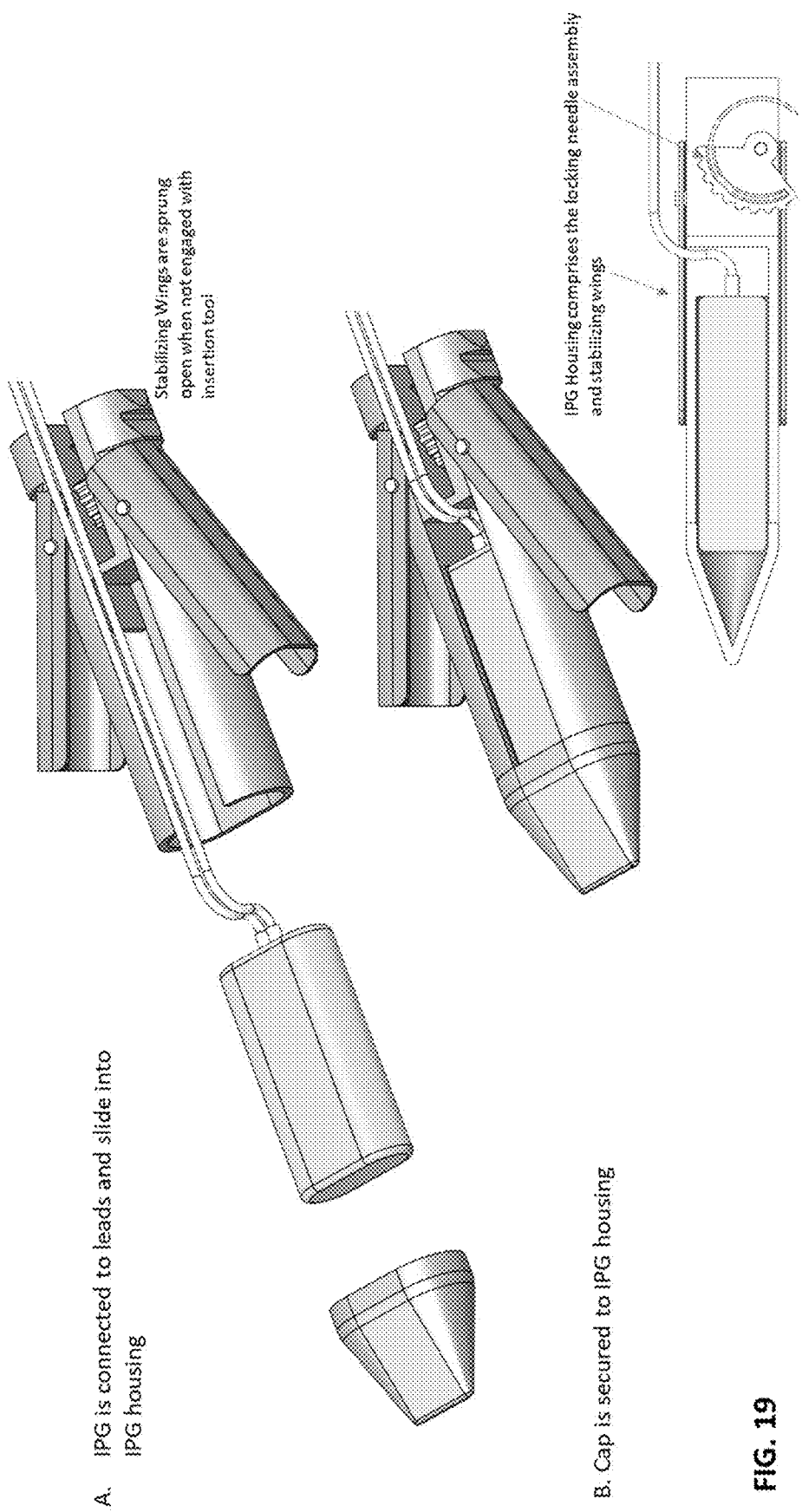
FIG. 19 shows a method of loading the internal pulse generator housing assembly into the insertion tool of an embodiment of the present invention.
Figure 19:
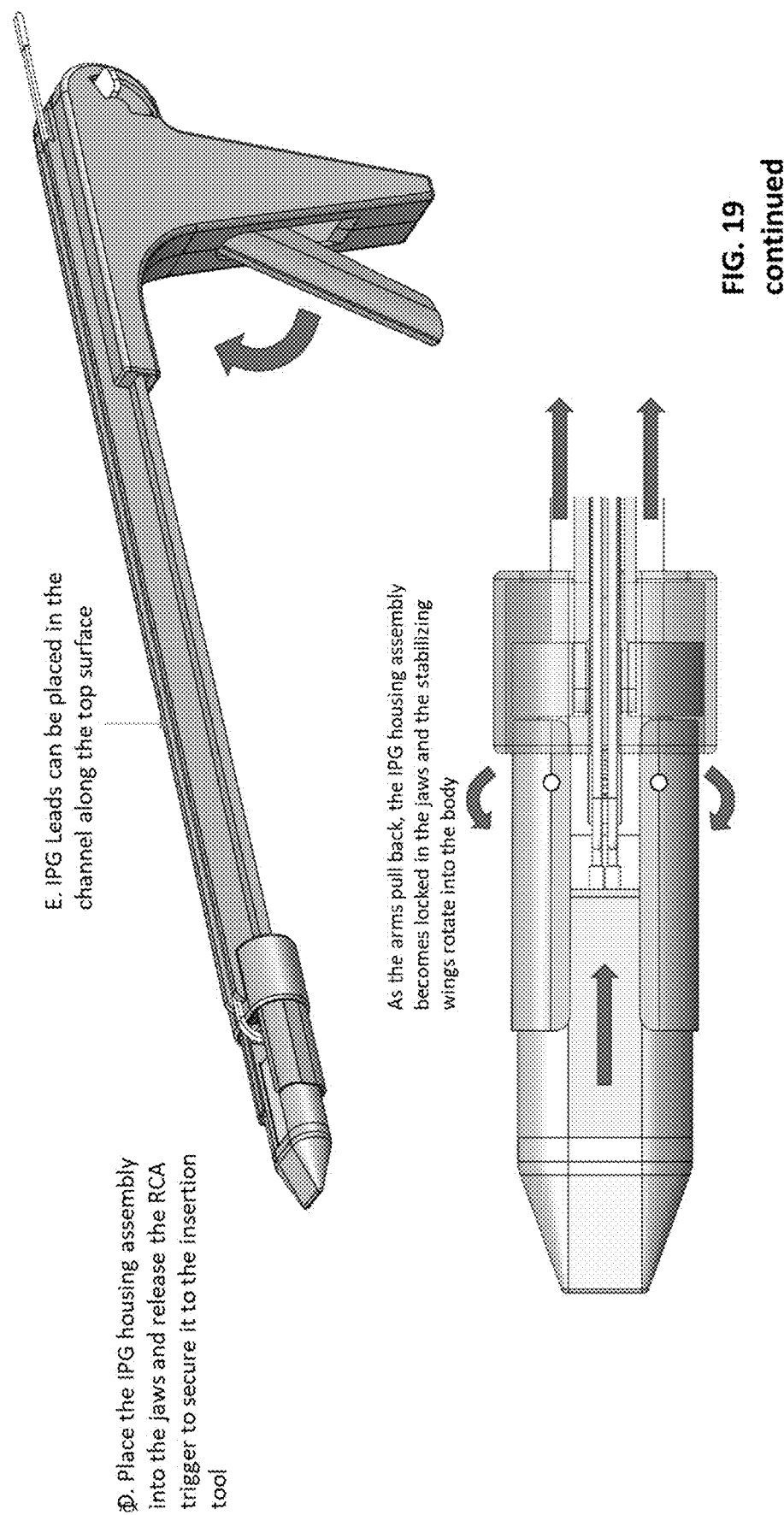
Figure 20:
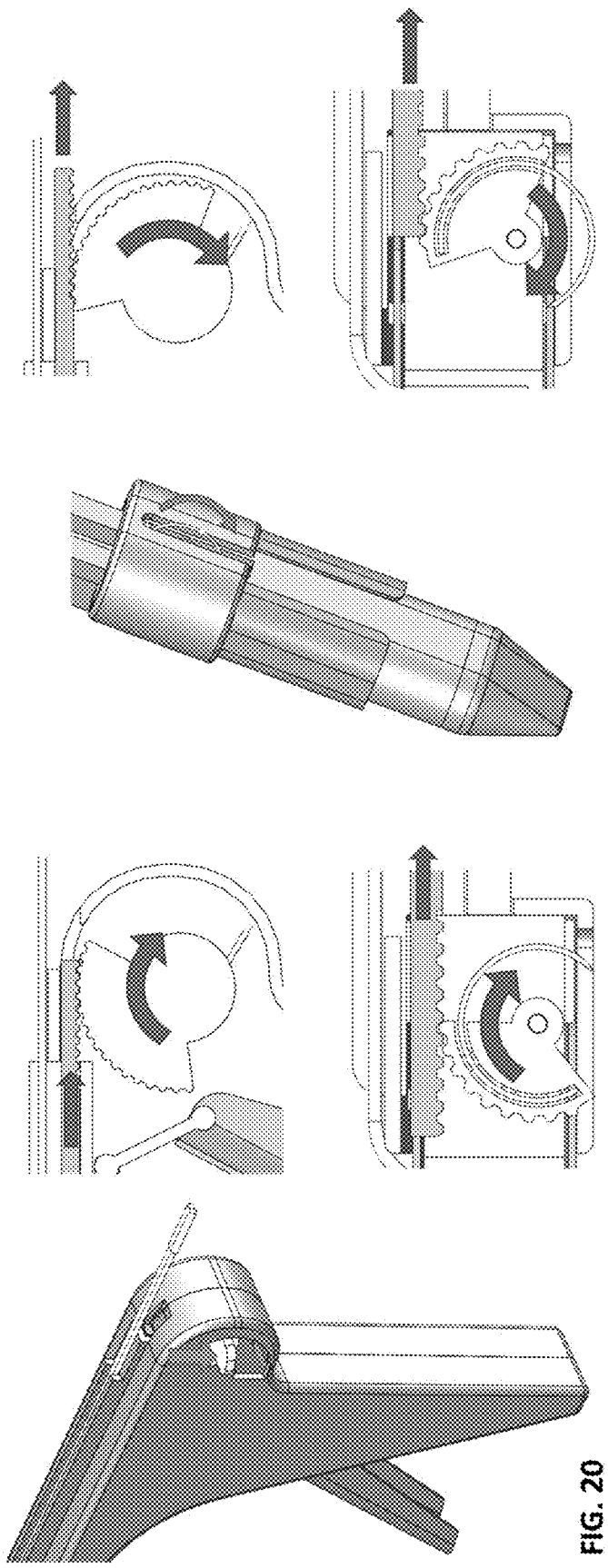
FIG. 20 shows a method of inserting the internal pulse generator into the body using the insertion tool of an embodiment of the present invention.
Figure 20:
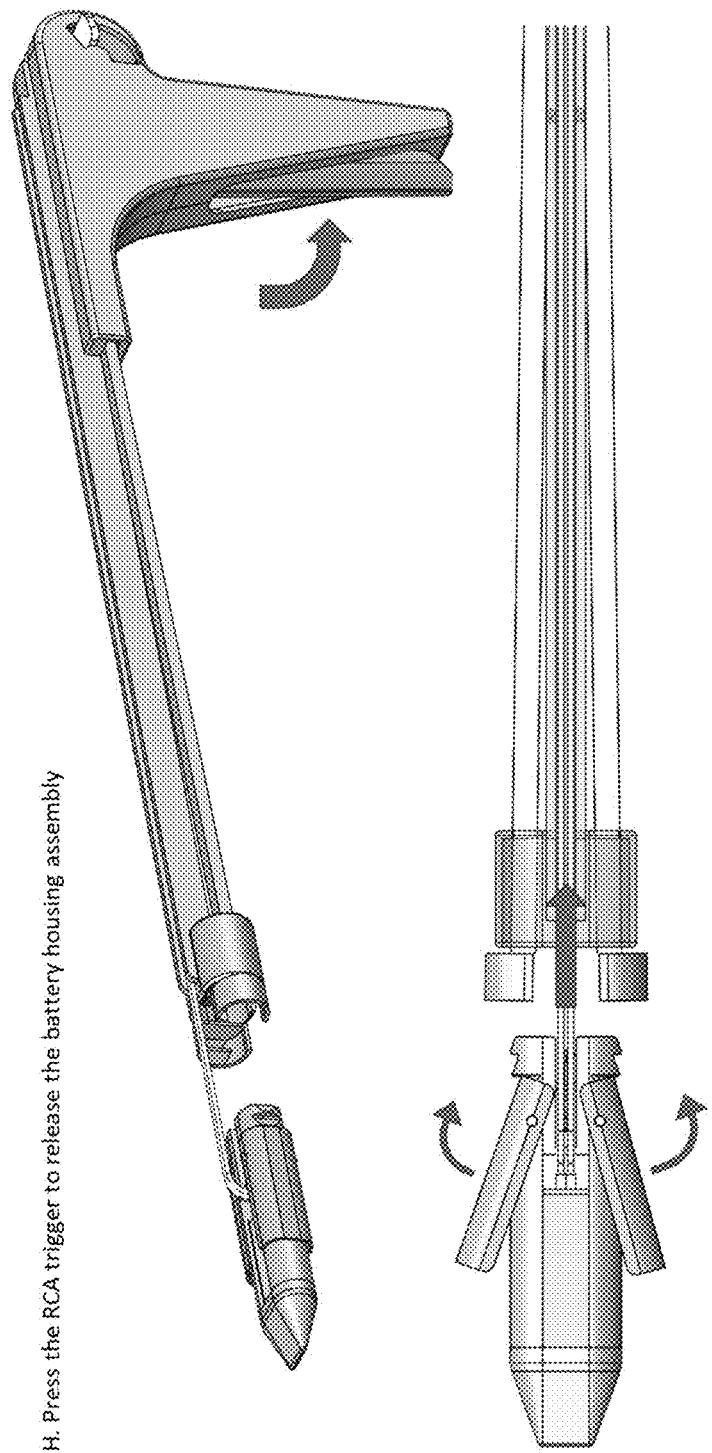

The use of the insertion tool is described in FIGS. 19-20. Briefly, A. The IPG is connected to leads and slide into IPG housing; B. A Cap/Dissector is secured to the IPG housing. The IPG in the IPG housing with the cap is the IPG housing assembly; C. The RCA trigger is pressed to move the arms forward and open the jaws; D. The IPG housing assembly is inserted into the jaws and the RCA trigger is released to secure the IPG housing assembly to the insertion tool; E. The IPG leads can be placed in the channel along the top surface; F. The front end (Cap) of the IPG housing assembly is used to dissect through the tissue layer to the desired position; G The LNA engagement trigger is pressed to lock the IPG housing assembly to the fascia layer; H. The RCA trigger is then pressed to release the IPG housing assembly. In certain embodiments, the tool adds one or more sutures to hold the IPG in place.

In certain embodiments, the IPG housing assembly is provided pre-assembled or as a unitary structure. In such embodiments, the IPG is connected to the IPG housing assembly and the continues as described above from step C.

In certain embodiments, the insertion tool is used to remove or reposition previously implanted IPGs. In particular, a previously implanted IPG assembly may be captured by the jaws of the insertion tool. In certain embodiments, the insertion tool includes a means to remove sutures.

STIMULATION SIGNAL GENERATION: Typically, neuromodulation systems have an internal pulse generator that generates a rectangular waveform A rectangular waveform has a known (and fixed) frequency spectrum for a given duty cycle. For example, a square wave with a fixed frequency has its highest peak at the fundamental frequency and the power is reduced by ¼ at each odd harmonic of the fundamental frequency. Sensory neurons throughout the central nervous system (such as the visual, auditory, and somatosensory cortex) are tuned to frequency, with different bandwidths of tuning, over a wide range of frequencies and bandwidths. It would therefore be beneficial to generate a waveform based on a specific predefined shape of the frequency spectrum.

A system for Frequency Domain Stimulation is described in which a distribution of frequencies is mathematically defined. One practical example is a modified gamma distribution, $$f(\omega) = \frac{\left[\frac{(-\omega-\mu)}{\beta}\right]^{\gamma-1} \cdot e^{\left[\frac{(-\omega-\mu)}{\beta}\right]}}{\beta \cdot \Gamma(\gamma)},$$

where $\omega$ is frequency, $-\mu$ is the highest frequency in the desired spectrum such that $\omega \leq -\mu$, $\gamma$ is the shape parameter, $\beta$ is the scale parameter ($\beta$, $\omega > 0$), and $\Gamma$ is the gamma function $\Gamma(a) \int_0^\infty t^{a-1} e^{-t} dt$.

Alternatively, a modified Weibull distribution may be used with the form:

$$f(\omega) = \begin{cases} \frac{k}{\lambda}\left(\frac{\mu-\omega}{\lambda}\right)^{k-1} e^{-\left(\frac{\mu-\omega}{\lambda}\right)^k}, & x \leq \mu \\ 0 & x > \mu \end{cases}$$

in which $\mu$ is the highest frequency, $k>0$ is the shape parameter, $\lambda>0$ is the scale parameter. This also allows patient programming in which the programmer may control the peak frequency, or the shape of the distribution. A signal is then computed that has the predefined. power spectral density by either a) assuming random phase with uniform distribution, or b) a fixed phase relationship between different frequencies. The steps of signal generation include a) creating an amplitude signal, 2) defining the phase, 3) generating the frequency function, and 4) taking the inverse Fourier transform. This would then generate the desired signal. These computations can be either done in the internal signal generator, or in the programming device with the actual signal being transmitted to the internal signal generator during programming sessions.

I claim:

1. A system comprising:
    a conduit,
    a keyed minimally-invasive (MIS) tube that is configured to be provided with the conduit, and
    a lead adaptor for placement of stimulator leads on neural elements during a spine surgery, and to access the stimulator leads via a minimally invasive surgery at a later date for stimulation of the stimulator leads with a pulse generator,
    wherein the conduit comprises:
        a conduit housing comprising at least two ports, wherein each of the at least two ports are configured to receive one of the stimulator leads so that the stimulator leads extend through the at least two ports; and
        a conduit anchor comprising a clamp for connection to a spine or spine instrumentation and a keyed seal ring to reversibly connect the keyed MIS tube in a specific orientation in said minimally invasive surgery;
    wherein the lead adaptor is configured for insertion through the keyed MIS tube and connection to the conduit, wherein the lead adaptor comprises a lead adaptor entry port for entry of pulse generator leads and a lead adaptor pin housing comprising contact pins, wherein the lead adaptor is configured to electrically connects—the pulse generator leads to the stimulator leads.

2. The system of claim 1, wherein a central hole is located between the at least two ports.

3. The system of claim 1, wherein the lead adaptor comprises:
    the lead adaptor entry port and the lead adaptor pin housing are configured to be connected together.

4. A kit for placement of stimulator leads on neural elements during a spine surgery, and to access the stimulator leads via a minimally invasive surgery (MIS) at a later date for stimulation of the stimulator leads with a pulse generator, the kit comprising:
    a. a conduit comprising:
        a conduit housing comprising at least two ports, wherein each of the at least two ports extend through one of the stimulator leads;
        a conduit anchor comprising a clamp for connection to a spine or spine instrumentation and a keyed seal ring to reversibly connect a keyed MIS tube in a specific orientation in the MIS;
    b. a lead adaptor configured for insertion through the keyed MIS tube and connection to the conduit, wherein the lead adaptor comprises a lead adaptor entry port for entry of pulse generator leads and a lead adaptor pin housing comprising contact pins.

5. The kit of claim 4, further comprising:
a conduit cap.
6. The kit of claim 4, further comprising:
a grooved applicator for placing the stimulator leads.
7. The kit of claim 4, further comprising:
one or more encircling clips to secure the stimulator leads.
8. The kit of claim 4, wherein a central hole is located between the at least two ports.
9. The kit of claim 4, wherein the lead adaptor comprises:
the lead adaptor entry port and the lead adaptor pin housing are configured to be connected together.

* * * * *